(12) United States Patent
Emgenbroich et al.

(10) Patent No.: US 12,427,119 B2
(45) Date of Patent: *Sep. 30, 2025

(54) TRANSDERMAL DELIVERY SYSTEM INCLUDING AN INTERFACE MEDIATOR

(71) Applicant: LTS Lohmann Therapie-Systeme AG, Andernach (DE)

(72) Inventors: Marco Emgenbroich, Rheinbach (DE); Johannes Josef Leonhard, Bendorf (DE); Kristina Kassner, Bergisch Gladbach (DE); Aurélia Lappert, Woluwe Saint Pierre (BE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,724

(22) Filed: Aug. 4, 2023

(65) Prior Publication Data

US 2024/0016757 A1    Jan. 18, 2024

Related U.S. Application Data

(63) Continuation of application No. 15/312,433, filed as application No. PCT/EP2015/061112 on May 20, 2015, now Pat. No. 11,752,110.

(30) Foreign Application Priority Data

May 20, 2014 (EP) .................................... 14169031

(51) Int. Cl.
*A61K 9/70* (2006.01)
*A61K 9/00* (2006.01)
(Continued)

(52) U.S. Cl.
CPC .......... *A61K 9/7069* (2013.01); *A61K 9/0014* (2013.01); *A61K 9/7038* (2013.01);
(Continued)

(58) Field of Classification Search
None
See application file for complete search history.

(56) References Cited

U.S. PATENT DOCUMENTS

| | | | |
|---|---|---|---|
| 4,769,028 | A | 9/1988 | Hoffman et al. |
| 4,814,168 | A | 3/1989 | Sablotsky et al. |

(Continued)

FOREIGN PATENT DOCUMENTS

| | | |
|---|---|---|
| CA | 2374930 A1 | 1/2001 |
| CN | 1462185 A | 12/2003 |

(Continued)

OTHER PUBLICATIONS

Chien, "Developmental Concepts and Practice in Transdermal Therapeutic Systems," Chapter 2 in Transdermal Controlled Systemic Medications, 1987, vol. 31, pp. 25-44.

(Continued)

*Primary Examiner* — Kyung S Chang
(74) *Attorney, Agent, or Firm* — ProPat, LLC; Cathy Moore

(57) ABSTRACT

The present invention relates to aransdermal therapeutic system for the transdermal administration of a systemically active agent having a self-adhesive layer structure. The transdermal therapeutic system includes (A) a backing layer, and (B) a dried biphasic layer. The dried biphasic layer has (a) an outer phase having a composition comprising 75% to 100% of a polymer or polymer mixture, and (b) an inner phase having a composition that includes at least one active agent. The inner phase forms dispersed deposits in the outer phase, with the dried biphasic layer including (c) from 0.1%

(Continued)

to 3.5% of an interface mediator other than silicone oil, with the interface mediator having with a kinematic viscosity of from 10 cSt to 100 000 cSt at 25° C.

19 Claims, 4 Drawing Sheets

(51) Int. Cl.
| | |
|---|---|
| *A61K 31/381* | (2006.01) |
| *A61K 47/02* | (2006.01) |
| *A61K 47/34* | (2017.01) |
| *A61P 21/00* | (2006.01) |
| *A61P 25/00* | (2006.01) |
| *A61P 25/10* | (2006.01) |
| *A61P 25/16* | (2006.01) |
| *A61P 25/20* | (2006.01) |
| *A61P 25/22* | (2006.01) |
| *A61P 25/24* | (2006.01) |
| *A61P 25/28* | (2006.01) |

(52) U.S. Cl.
CPC ............ *A61K 31/381* (2013.01); *A61K 47/02* (2013.01); *A61K 47/34* (2013.01); *A61P 21/00* (2018.01); *A61P 25/00* (2018.01); *A61P 25/16* (2018.01); *A61P 25/20* (2018.01); *A61P 25/22* (2018.01); *A61P 25/24* (2018.01); *A61P 25/28* (2018.01)

(56) References Cited

U.S. PATENT DOCUMENTS

| | | | |
|---|---|---|---|
| 4,994,267 | A | 2/1991 | Sablotsky |
| 4,994,278 | A | 2/1991 | Sablotsky et al. |
| 5,032,207 | A | 7/1991 | Sablotsky et al. |
| 5,300,291 | A | 4/1994 | Sablotsky et al. |
| 5,405,486 | A | 4/1995 | Sablotsky et al. |
| 5,474,783 | A | 12/1995 | Miranda et al. |
| 5,656,285 | A | 8/1997 | Sablotsky et al. |
| 5,656,286 | A | 8/1997 | Miranda et al. |
| 5,686,099 | A | 11/1997 | Sablotsky et al. |
| 5,719,197 | A | 2/1998 | Kanios et al. |
| 5,958,446 | A | 9/1999 | Miranda et al. |
| 6,024,976 | A | 2/2000 | Miranda et al. |
| 6,221,383 | B1 | 4/2001 | Miranda et al. |
| 6,235,306 | B1 | 5/2001 | Miranda et al. |
| 6,884,434 | B1 | 4/2005 | Müller et al. |
| 7,383,083 | B2 | 6/2008 | Fischer et al. |
| 7,847,014 | B2 | 12/2010 | Koch et al. |
| 8,211,462 | B2 | 7/2012 | Breitenbach et al. |
| 8,246,979 | B2 | 8/2012 | Schacht et al. |
| 9,265,752 | B2 | 2/2016 | Wang et al. |
| 2001/0053383 | A1 | 12/2001 | Miranda et al. |
| 2003/0026830 | A1 | 2/2003 | Lauterback et al. |
| 2003/0060479 | A1 | 3/2003 | Brown et al. |
| 2003/0149394 | A1 | 8/2003 | Joshi |
| 2003/0198622 | A1 | 10/2003 | Van Osdol et al. |
| 2004/0131897 | A1 | 7/2004 | Jenson et al. |
| 2004/0137045 | A1 | 7/2004 | Breitenbach et al. |
| 2004/0138299 | A1 | 7/2004 | Cahill et al. |
| 2004/0234583 | A1 | 11/2004 | Müller |
| 2005/0019385 | A1 | 1/2005 | Houze |
| 2005/0175678 | A1 | 8/2005 | Breitenbach |
| 2005/0202073 | A1 | 9/2005 | Jackson et al. |
| 2005/0260254 | A1 | 11/2005 | Breitenbach et al. |
| 2006/0263419 | A1 | 11/2006 | Wolff |
| 2009/0048556 | A1 | 2/2009 | Durand |
| 2009/0299304 | A1 | 12/2009 | Tang |
| 2010/0119585 | A1 | 5/2010 | Hille et al. |
| 2010/0286590 | A1 | 11/2010 | Durand |
| 2010/0311661 | A1 | 12/2010 | Küllertz |
| 2011/0027345 | A1 | 2/2011 | Wang et al. |
| 2011/0104244 | A1 | 5/2011 | Hille et al. |
| 2014/0046279 | A1 | 2/2014 | Leonhard et al. |
| 2015/0290142 | A1 | 10/2015 | Cawello et al. |

FOREIGN PATENT DOCUMENTS

| | | |
|---|---|---|
| CN | 1606435 A | 4/2005 |
| CN | 1671375 A | 9/2005 |
| CN | 1897935 A | 1/2007 |
| CN | 101146524 A | 3/2008 |
| CN | 101601664 A | 12/2009 |
| CN | 102458397 A | 5/2012 |
| CN | 102770128 A | 11/2012 |
| DE | 102012013421 A1 | 1/2014 |
| EP | 1 669 063 A1 | 6/2006 |
| EP | 2 177 217 A1 | 4/2010 |
| EP | 2 292 219 A1 | 3/2011 |
| JP | 1998509621 A | 9/1998 |
| JP | 2003-526656 A | 9/2003 |
| JP | 2004-521085 A | 7/2004 |
| JP | 2004-525164 A | 8/2004 |
| JP | 2004-528359 A | 9/2004 |
| JP | 2005-528425 A | 9/2005 |
| JP | 2005-535686 A | 11/2005 |
| JP | 2005535687 A | 11/2005 |
| JP | 2006508908 A | 3/2006 |
| JP | 2006515952 A | 6/2006 |
| JP | 2006178807 A | 7/2006 |
| JP | 2007-528392 A | 10/2007 |
| JP | 2009297808 A | 12/2009 |
| JP | 2010-106037 A | 5/2010 |
| JP | 2010158554 A | 7/2010 |
| JP | 2010536434 A | 12/2010 |
| JP | 2011-500647 A | 1/2011 |
| JP | 2011-504902 A | 2/2011 |
| JP | 2011-526592 A | 10/2011 |
| JP | 2012501799 A | 1/2012 |
| JP | 2012-504609 A | 2/2012 |
| JP | 2012-509276 A | 4/2012 |
| JP | 2013510805 A | 3/2013 |
| JP | 2013515041 A | 5/2013 |
| WO | 1989/10108 A1 | 11/1989 |
| WO | 1991/14463 A1 | 10/1991 |
| WO | 1992/19451 A1 | 11/1992 |
| WO | 1993/00058 A1 | 1/1993 |
| WO | 1995/18603 A1 | 7/1995 |
| WO | 1999/049852 A1 | 10/1999 |
| WO | 2000/44437 A1 | 8/2000 |
| WO | 2001/01967 A1 | 1/2001 |
| WO | 2002/015903 A2 | 2/2002 |
| WO | 2002/089777 A1 | 11/2002 |
| WO | 2003/015678 A1 | 2/2003 |
| WO | 2003/092677 A1 | 11/2003 |
| WO | 2004/012721 A2 | 2/2004 |
| WO | 2004/012730 A1 | 2/2004 |
| WO | 2004/050083 A1 | 6/2004 |
| WO | 2005/009424 A1 | 2/2005 |
| WO | 2005/063236 A1 | 7/2005 |
| WO | 2005/063237 A1 | 7/2005 |
| WO | 2005/092331 A1 | 10/2005 |
| WO | 2005/119610 A1 | 12/2005 |
| WO | 2008/061639 A1 | 5/2008 |
| WO | 2009/068520 A2 | 6/2009 |
| WO | 2010/042152 A2 | 4/2010 |
| WO | 2011/057714 A3 | 5/2011 |
| WO | 2011/076879 A1 | 6/2011 |
| WO | 2012/071175 A1 | 5/2012 |
| WO | 2012/084969 A1 | 6/2012 |
| WO | 2013/075822 A1 | 5/2013 |
| WO | 2013/075823 A1 | 5/2013 |
| WO | 2013/088254 A1 | 6/2013 |
| WO | 2014/079573 A1 | 5/2014 |
| WO | 2014/195352 A1 | 12/2014 |

OTHER PUBLICATIONS

JP Application No. 2018-147720 First Office Action, which corresponds to U.S. Appl. No. 16/009,613.

(56) References Cited

OTHER PUBLICATIONS

JP Application No. 2016-522618 First Office Action, which corresponds to U.S. Appl. No. 16/009,613.
JP Application No. 2016-522618 Second Office Action, which corresponds to U.S. Appl. No. 16/009,613.
Office Actions in U.S. Appl. No. 14/443,210.
Office Actions in U.S. Appl. No. 14/975,478.
Office Actions in U.S. Appl. No. 15/312,433.
Office Actions in U.S. Appl. No. 15/312,509.
Office Actions in U.S. Appl. No. 16/009,613.
International Preliminary Report on Patentability, PCT/EP2013/003515, which corresponds to U.S. Appl. No. 14/443,210.
International Search Report, PCT/EP2013/003515, which corresponds to U.S. Appl. No. 14/443,210.
Dow Corning: Amine-Compatible Silicone Adhesives, Jul. 28, 2008.
Henkel Corporation, "DURO-TAK and GELVA Transdermal Pressure Sensitive Adhesives," Product Selection Guide, Sep. 2013.
H.F. Hammond in D. Satas "Handbook of Pressure Sensitive Adhesive Techology" (1989) 2nd ed., Chapter 4, Van Nostrand Reinhold, New York, p. 38.
Kandavilli, Sateesh et al., "Polymers in Transdermal Drug Delivery Systems," Pharmaceutical Technology, May 2002, pp. 62-80.
Fachinformation Neupro (Aug. 2011) with English Translation.
www.ucb.com/investors/Our-equity-story/Neupro(Jan. 6, 2016).
"Pressure Sensitive Tack of Adhesives Using an Inverted Probe Machine" ASTM D2979-71 (1982).
K.L. Ulman and R.P. Sweet, "The Correlation of Tape Properties and Rheology" (1998), Information Brochure, Dow Corning Corp., USA.
Chinese Search Report for the CN Application 201380054953.X, which corresponds to U.S. Appl. No. 14/443,210.
Dow Corning 360 Medical Fluid, (retrieved from on-line website; https://www.b2bcomposites.com/msds/ted/71115.pdf, pp. 1-7, 2010).
International Search Report, PCT/EP2015/061099, which corresponds to U.S. Appl. No. 15/312,509.
International Search Report, PCT/EP2015/061112, which corresponds to U.S. Appl. No. 15/312,433.
International Preliminary Report on Patentability, PCT/EP2014/064166, which corresponds to U.S. Appl. No. 14/975,478.
Dow Corning® product information sheet 360 Medical Fluid, Aug. 10, 2015.
Dupont product information sheet Liveo TM BIO-PSA 7-4502, rev. Sep. 3, 2020.

TRANSDERMAL DELIVERY SYSTEM INCLUDING AN INTERFACE MEDIATOR

CROSS-REFERENCE TO RELATED APPLICATIONS

This application claims priority to U.S. patent application Ser. No. 15/312,433, filed Nov. 18, 2016, which has been allowed, and International Patent Application No. PCT/EP2015/061112, filed May 20, 2015, which claims priority to European Patent Application No. 14169031.3 filed May 20, 2014. Each of the foregoing applications, i.e. U.S. patent application Ser. No. 15/312,433; International Patent Application No. PCT/EP2015/061112 and European Patent Application No. 14169031.3, are hereby incorporated herein by reference in their entirety.

TECHNICAL FIELD OF THE INVENTION

The present invention relates to a transdermal therapeutic system (TTS) for the transdermal administration of a systemically active agent, processes of manufacture, and uses thereof.

BACKGROUND OF THE INVENTION

Transdermal therapeutic systems (TTS) for the transdermal administration of systemically active agents have several advantages over other application systems. In comparison to oral dosage forms, for example, fewer side effects are observed. Furthermore, constant drug levels in the patient can be achieved more easily. Due to the simple mode of application more convenience is accomplished for the patient. In particular, longer administration periods on the skin of human patients are beneficial for the compliance and for constant therapeutic drug levels. As a consequence of longer administration periods, a higher loading of the active agent is required in order to be able to provide therapeutically effective amounts of the active agent over the whole administration period. However, an increase of the active agent loading seems limited, in particular in solvent-based transdermal therapeutic systems. In solvent-based biphasic systems which comprise the active agent in a separate phase dispersed in a matrix, an increased active agent concentration in the TTS matrix may result e.g., in crystallization of the active agent during storage which jeopardizes the therapeutic success due to insufficient permeation rates of the remaining active agent available for skin absorption. Furthermore, an increased concentration of active agent-containing phase in the biphasic system may lead to coalescence of the dispersed phase. In this context, it was found that the size of the dispersed phase including the active agent has an influence on the drug release. A TTS manufactured with large active agent-containing droplets in its biphasic layer may lead to e.g., a more fluctuating drug release or to dose dumping. Smaller droplets provide reliable permeation rates with minimum fluctuation. It is thus believed that by reducing the droplet size of the active-agent containing phase of a biphasic system, a stabilization of the system is achieved, in particular for biphasic systems with an increased drug loading.

So far, a reduction of the droplet sizes in a solvent-based biphasic system is solely achieved by applying mechanical force to a biphasic coating mixture. Therefore, there remains room for improvement of such transdermal therapeutic systems, and in processes for making them.

OBJECTS AND SUMMARY OF ADVANTAGEOUS EMBODIMENTS OF THE INVENTION

It is an object of the present invention to provide a transdermal therapeutic system for the transdermal administration of a systemically active agent which provides long-term stability.

It is an object of the present invention to provide a transdermal therapeutic system for the transdermal administration of a systemically active agent providing a continuous administration of therapeutically effective amounts of the active agent for 1 to 7 days during an administration period to the skin of the patient of 1 to 7 days (e.g., 7 days).

It is an object of the present invention to provide a transdermal therapeutic system for the transdermal administration of a systemically active agent providing a reduced fluctuation of the therapeutically effective permeation rate of the active agent for 1 to 7 days during an administration period to the skin of the patient of 1 to 7 days (e.g., 7 days).

It is a further object of the present invention to provide a transdermal therapeutic system for the transdermal administration of a systemically active agent which complies with the needs of a convenient application in view of skin tolerance, size and thickness and can easily and cost-effectively be prepared.

It is also an object of the present invention to provide a method of manufacture of an active agent-containing dried biphasic layer with a small maximum droplet size.

These objects and others are accomplished by the present invention, which according to one aspect relates to a transdermal therapeutic system for the transdermal administration of a systemically active agent comprising a self-adhesive layer structure, comprising A) a backing layer, and
B) a dried biphasic layer, the dried biphasic layer having
   a) an outer phase having a composition comprising 75% to 100% of a polymer or polymer mixture, and
   b) an inner phase having a composition comprising at least one active agent, wherein the inner phase forms dispersed deposits in the outer phase,
   and
   c) 0.1% to 3.5% of an interface mediator with a kinematic viscosity of from 10 cSt to 100 000 cSt at 25° C.,
and
C) optionally an additional skin contact layer,
in particular for use in a method of treatment, wherein therapeutically effective amounts of the systemically active agent are provided for 1 to 7 days by said transdermal therapeutic system during an administration period of 1 to 7 days.

According to another specific aspect the invention relates to a transdermal therapeutic system for the transdermal administration of rotigotine containing 2.0 mg/cm$^2$ to 4.0 mg/cm$^2$ rotigotine base in a self-adhesive layer structure, comprising A) a backing layer, and
B) a dried biphasic layer, the dried biphasic layer having
   a) an outer phase having a composition comprising 75% to 100% of pressure-sensitive adhesive polysiloxane(s), and
   b) an inner phase having a composition comprising rotigotine, wherein the inner phase forms dispersed deposits in the outer phase,
and
c) 0.1% to 3.5% of a silicone oil with a kinematic viscosity of from 10 cSt to 100 000 cSt at 25° C., and
and
C) optionally an additional skin contact layer,
in particular for use in a method of treatment, wherein therapeutically effective amounts of the rotigotine base are provided for 1 to 7 days by said transdermal therapeutic system during an administration period of 1 to 7 days, in particular for use in a method of treating patients suffering from Parkinson's disease, Parkinson's plus syndrome, depression, anxiety, attention deficit/hyperactivity syndrome ("ADHS"), fibromyalgia, the restless-legs syndrome and for use in the treatment or prevention of dopaminergic neuron loss or the treatment or prevention of cognitive disorders, dementia or lewy body disease.

According to another aspect the invention relates to a transdermal therapeutic system for the transdermal administration of rotigotine containing 2.0 mg/cm$^2$ to 3.0 mg/cm$^2$ rotigotine base in a self-adhesive layer structure, comprising
A) a backing layer, and
B) a dried biphasic layer, the dried biphasic layer having
 a) an outer phase having a composition comprising 75% to 100% of pressure-sensitive adhesive polysiloxane(s), and
 b) an inner phase having a composition comprising rotigotine,
 wherein the inner phase forms dispersed deposits in the outer phase,
 and
 c) 0.1% to 3.5% of a silicone oil with a kinematic viscosity of from 10 cSt to 100 000 cSt at 25° C., and
and
C) optionally an additional skin contact layer,
in particular for use in a method of treatment, wherein therapeutically effective amounts of the rotigotine base are provided for 1 to 7 days by said transdermal therapeutic system during an administration period of 1 to 7 days, in particular for use in a method of treating patients suffering from Parkinson's disease, Parkinson's plus syndrome, depression, anxiety, ADHS, fibromyalgia, the restless-legs syndrome and for use in the treatment or prevention of dopaminergic neuron loss or the treatment or prevention of cognitive disorders, dementia or lewy body disease.

According to one specific aspect the invention relates to a method of manufacture of an active agent-containing dried biphasic layer comprising the steps of:
(1) preparing a biphasic coating mixture having an inner phase dispersed in an outer phase:
 (a) the inner phase comprising the active agent,
 (b) the outer phase comprising a polymer or polymer mixture,
 wherein the biphasic coating mixture comprises solvents in sufficient amounts to provide for a viscosity of the coating mixture suitable for coating,
(2) adding to said biphasic coating mixture an interface mediator, and mixing said coating mixture to provide a suitable dispersion of the inner phase in the outer phase,
(3) coating said coating mixture on a film to provide a layer of said solvent-containing mixture,
(4) evaporating said solvents to provide a dried layer with a coating weight to provide said active agent-containing dried biphasic layer with the desired area weight,
(5) optionally laminating two or more of said dried layers to provide said active agent-containing dried biphasic layer with the desired area weight.

According to a certain embodiment, the invention relates to a dried biphasic layer obtainable by the method of manufacture described in the previous paragraph.

According to another specific aspect the invention relates to a method of manufacture of a transdermal therapeutic system comprising an active agent-containing dried biphasic layer for the transdermal administration of a systemically active agent in accordance with the invention, comprising the steps of:
(1) preparing a biphasic coating mixture having an inner phase dispersed in an outer phase:
 (a) the inner phase comprising the active agent,
 (b) the outer phase comprising a polymer or polymer mixture, wherein the biphasic coating mixture comprises solvents in sufficient amounts to provide for a viscosity of the coating mixture suitable for coating,
(2) adding to said biphasic coating mixture an interface mediator, and mixing said coating mixture to provide a suitable dispersion of the inner phase in the outer phase,
(3) coating said coating mixture on a film to provide a layer of said solvent-containing mixture,
(4) evaporating said solvents to provide a dried layer with a coating weight to provide an active agent-containing dried biphasic layer with the desired area weight,
(5) optionally laminating two or more of said dried layers to provide an active agent-containing dried biphasic layer with the desired area weight,
(6) laminating said active agent-containing dried biphasic layer to a backing layer,
(7) optionally laminating said active agent-containing biphasic layer to an additional skin contact layer,
preferably wherein for the production of the dried biphasic layer and optionally the additional skin contact layer a pressure-sensitive adhesive mixture of pressure-sensitive adhesive polysiloxanes in heptanes or ethyl acetate is used.

According to one aspect the invention relates to the use of a silicone oil as interface mediator in a transdermal therapeutic system with an active agent-containing dried biphasic layer having a hydrophilic inner phase and a hydrophobic outer phase for controlling the maximum droplet size of the inner phase of said dried biphasic layer, in particular in a transdermal therapeutic system wherein the active agent is rotigotine base and is present in the dried biphasic layer in an amount of 16% to 26% of the dried biphasic layer.

According to a further aspect the invention relates to the use of an interface mediator to reduce the maximum droplet size of the inner phase in form of dispersed deposits in the outer phase of a dried biphasic layer in a transdermal therapeutic system as described above.

Within the meaning of this invention, the term "transdermal therapeutic system" (or TTS) refers to a system by which the active agent (e.g., rotigotine) is administered systemically and in particular refers to the entire individual unit that is applied to the skin of a patient, and which comprises a therapeutically effective amount of a systemically active agent in a self-adhesive layer structure and optionally an additional larger active-free self-adhesive layer structure (overlaying adhesive) on top of the active agent-containing self-adhesive layer structure. During storage, such a TTS is normally located on a detachable protective layer from which it is removed immediately before application to the surface of the patient's skin. A TTS protected this way may be stored in a blister pack or a side sealed bag.

Within the meaning of this invention, the terms "active", "active agent" are used synonymously. Unless otherwise indicated the amounts of active agent in the TTS relate to the amount of active agent before administration of the TTS. The amounts of active agent in the TTS after administration are referred to as residual amounts.

Within the meaning of this invention, the terms "active agent-containing self-adhesive layer structure" and "comprising the active agent in a self-adhesive layer structure" have the same meaning and refer to the active agent-containing structure providing the area of release of the active agent.

Within the meaning of this invention, the term "biphasic" refers to a system of two distinguishable, e.g., visually distinguishable, areas, an outer phase and an inner phase, wherein the inner phase is in form of dispersed deposits within the outer phase. Such deposits are e.g., solid solution droplets. Deposits that are visually distinguishable may be identified by use of a microscope.

Within the meaning of this invention, the term "dried biphasic layer" refers to a biphasic layer obtained from a solvent-containing coating mixture after coating on a film and evaporating the solvents (solvent-based layer) and is to be distinguished from a biphasic layer obtained from a hot-melt coating mixture (hot-melt-based layer).

Within the meaning of this invention, the term "polymer mixture" includes mixtures of polymers comprising the same monomer(s) but providing different grades. Polymers of different grades are polymers which are distinguishable by different properties (e.g., the viscosity) and are usually commercially available under different trademarks. E.g., the commercially available products KOLLIDON® 90 and KOLLIDON® 30 provide individual grades of polyvinylpyrrolidone, a polymer of the monomer vinylpyrrolidone; the commercially available products DOW CORNING® BIO-PSA 7-4201 and BIO-PSA 7-4301 provide individual grades of pressure-sensitive adhesive polysiloxane.

Within the meaning of this invention, the term "interface mediator" refers to a substance that promotes a maximum separation of an inner phase in an outer phase to allow the inner phase to be uniformly dispersed without exhibiting surface activity. The interface mediator enhances the compatibility of the two separate phases by filling cavities at the interface between the two phases. As a result, the inner phase forms dispersed deposits with a minimum size which provide an increase of the dynamic viscosity of the biphasic system. The increased dynamic viscosity further provides a reduced attempt of the inner phase to coalesce and thereby stabilizes the biphasic system.

Within the meaning of this invention, the term "silicone oil" refers to any liquid polymerized siloxane with organic side chains.

Within the meaning of this invention, the term "solid solution" refers to a mixture of active agent (e.g., rotigotine) and the polymer mixture to provide a single homogeneous phase in form of a solid-state solution.

Within the meaning of this invention, the term "pressure-sensitive adhesive" refers to a composition that in particular adheres with finger pressure, is permanently tacky, exerts a strong holding force and should be removable from smooth surface without leaving a residue. The pressure-sensitive adhesive properties of the pressure-sensitive adhesive composition are based on suitable tackifiers, or on a polymer or polymer mixture which is a/are pressure-sensitive adhesive polymer(s), or on both. Pressure-sensitive adhesive polymer(s) are available in solid form or in a mixture with a suitable solvent (e.g., heptane or ethyl acetate). According to a certain embodiment, the polymer or polymer mixture is a/are pressure-sensitive adhesive polysiloxane(s). Examples of useful pressure-sensitive adhesive polysiloxanes which are commercially available include the standard BIO-PSA series (7-4400, 7-4500 and 7-4600 series), the amine compatible (endcapped) BIO-PSA series (7-4100, 7-4200 and 7-4300 series), and the SOFT SKIN ADHESIVES® series (7-9800) manufactured by Dow Corning. Preferred pressure-sensitive polysiloxanes are heptane- and ethyl acetate-solvated pressure-sensitive adhesive polysiloxanes including BIO-PSA 7-4201, BIO-PSA 7-4301, BIO-PSA 7-4202, and BIO-PSA 7-4302.

Within the meaning of this invention, the term "pressure-sensitive adhesive mixture" refers to a pressure-sensitive adhesive polymer or pressure-sensitive adhesive polymers at least in mixture with a solvent (e.g., heptane or ethyl acetate).

Within the meaning of this invention, the term "polyvinylpyrrolidone" refers to polyvinylpyrrolidone which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include KOLLIDON® 12 PF, KOLLIDON® 17 PF, KOLLIDON® 25, KOLLIDON® 30 and KOLLIDON® 90 F supplied by BASF. The different grades of KOLLIDON® are defined in terms of the K-Value reflecting the average molecular weight of the polyvinylpyrrolidone grades. KOLLIDON® 12 PF is characterized by a K-Value range of 10.2 to 13.8, corresponding to a nominal K-Value of 12. KOLLIDON® 17 PF is characterized by a K-Value range of 15.3 to 18.4, corresponding to a nominal K-Value of 17. KOLLIDON® 25 is characterized by a K-Value range of 22.5 to 27.0, corresponding to a nominal K-Value of 25, KOLLIDON® 30 is characterized by a K-Value range of 27.0 to 32.4, corresponding to a nominal K-Value of 30. KOLLIDON® 90 F is characterized by a K-Value range of 81.0 to 97.2, corresponding to a nominal K-Value of 90. A preferred KOLLIDON® grade is KOLLIDON® 90 F.

Within the meaning of this invention, the term "K-Value" refers to a value calculated from the relative viscosity of polyvinylpyrrolidone in water according to the European Pharmacopoeia (Ph.Eur.) and USP monographs for "Povidone".

Within the meaning of this invention, the term "skin contact layer" refers to the part of the TTS which is an additional layer (in addition to the active agent-containing dried biphasic layer) and is in direct contact with the skin of the patient during administration. The sizes of an additional skin contact layer and the active agent-containing self-adhesive layer structure are co-extensive and correspond to the area of release.

Within the meaning of this invention, the term "additional larger active agent-free self-adhesive layer structure" (overlaying adhesive) refers to a self-adhesive layer structure that is free of active agent and larger in area than the active agent-containing structure and providing additional area adhering to the skin, but no area of release of the active agent, and enhancing thereby the overall adhesive properties of the TTS.

Within the meaning of this invention, the term "area weight" refers to the dry weight of an individual layer or the sum of individual layers, except backing layer and release liner, and is provided in g/m². The area weight may be the coating weight of a layer, or the sum of the coating weights of individual layers. Amounts of active agent or polymer in a layer provided in mg/cm² or % refer to or are based on the area weight of the layer. If not indicated otherwise "%" refers to weight-%.

DETAILED DESCRIPTION OF ADVANTAGEOUS EMBODIMENTS

TTS Structure

Figure 1:
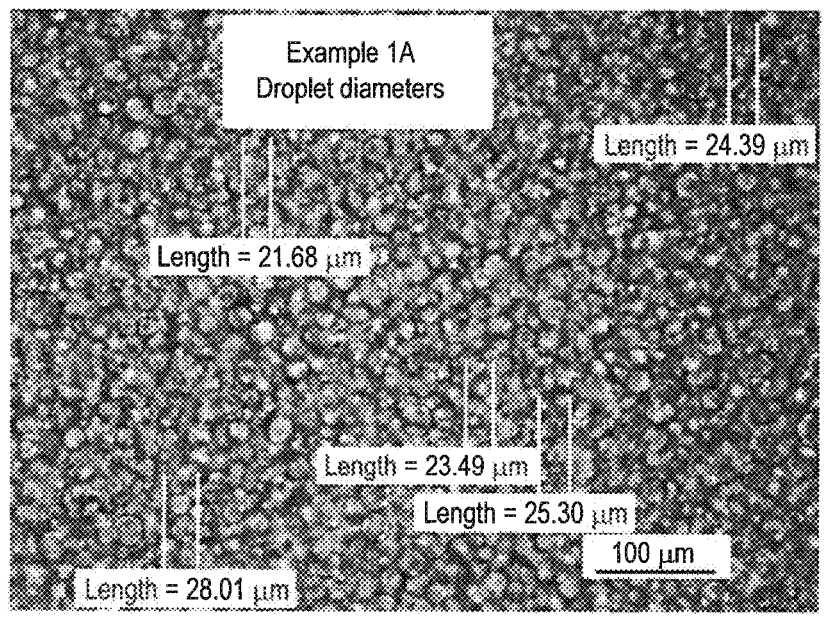
FIG. 1 depicts the rotigotine-containing biphasic coating mixture of Example 1A.
Figure 2:
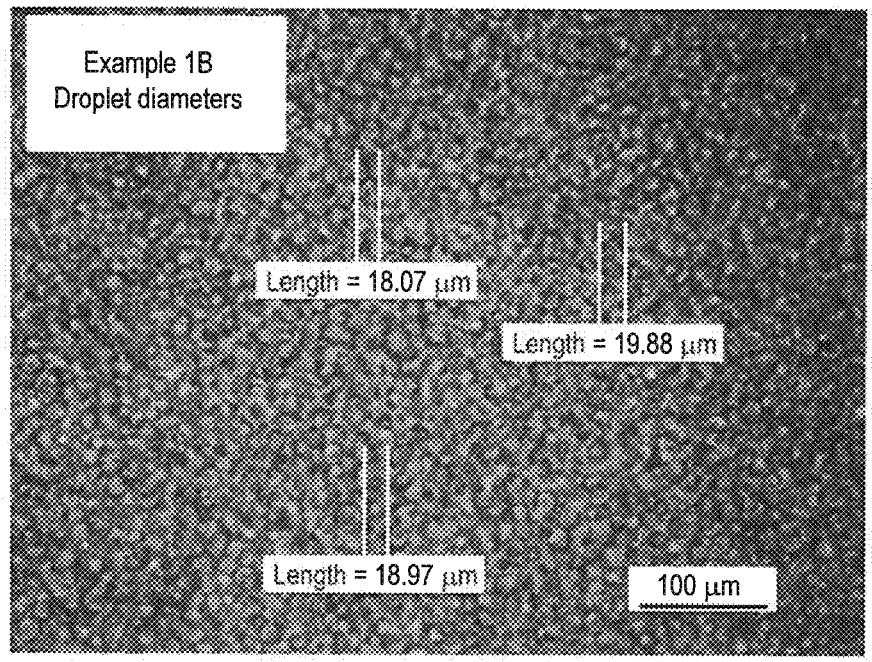
FIG. 2 depicts the rotigotine-containing biphasic coating mixture of Example 1B with 1% silicone oil (DOW CORNING® Medical Fluid 100 cSt).
Figure 3:
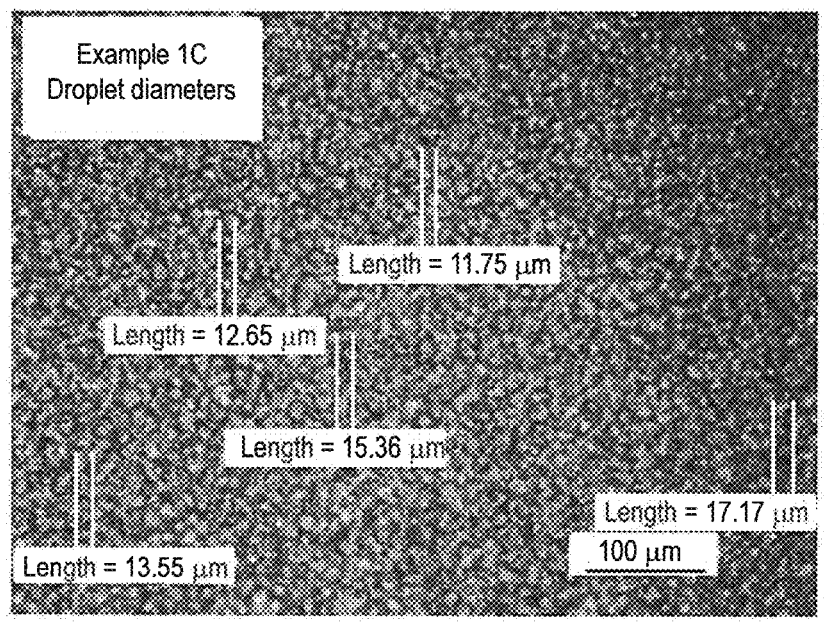
FIG. 3 depicts the rotigotine-containing biphasic coating mixture of Example 1C with 1% silicone oil (DOW CORNING® Medical Fluid 350 cSt).
Figure 4:
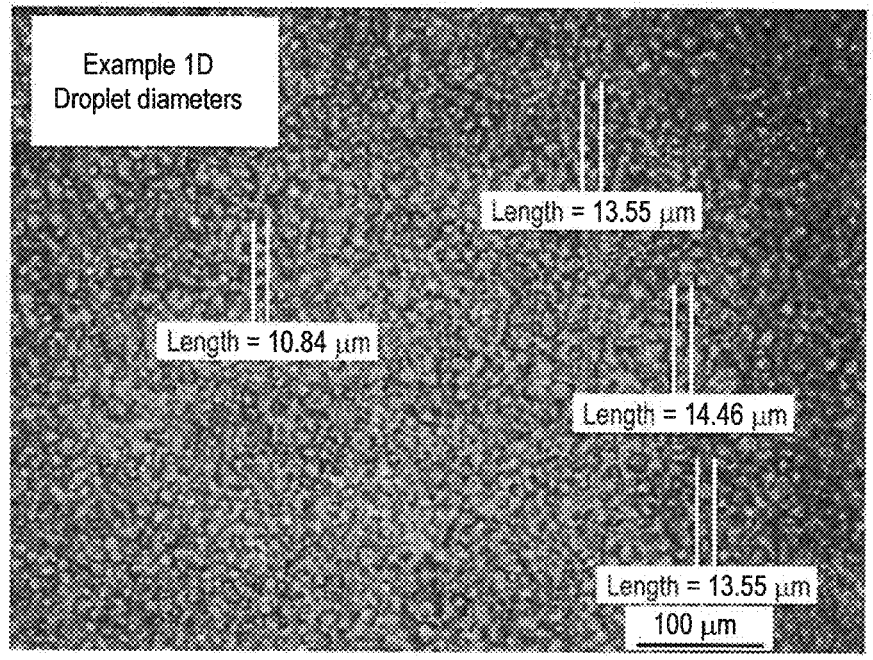
FIG. 4 depicts the rotigotine-containing biphasic coating mixture of Example 1D with 1% silicone oil (DOW CORNING® Medical Fluid 1000 cSt).
Figure 5:
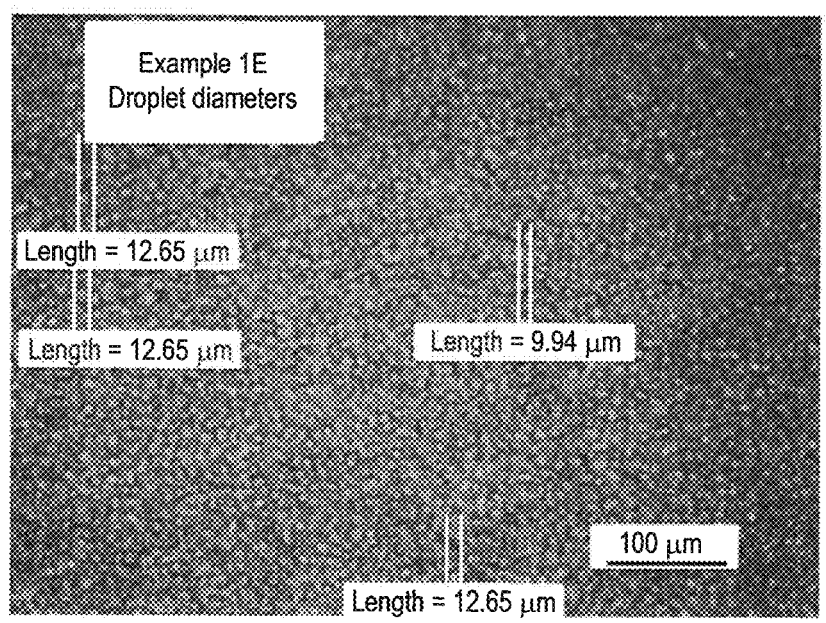
FIG. 5 depicts the rotigotine-containing biphasic coating mixture of Example 1E with 1% silicone oil (DOW CORNING® Medical Fluid 12500 cSt).

According to a certain embodiment of the invention the transdermal therapeutic system for the transdermal administration of a systemically active agent comprising a self-adhesive layer structure, comprising
A) a backing layer, and
B) a dried biphasic layer, the dried biphasic layer having
   a) an outer phase having a composition comprising 75% to 100% a polymer or polymer mixture, and
   b) an inner phase having a composition comprising at least one active agent,
   wherein the inner phase forms dispersed deposits in the outer phase,
   and
   c) 0.1% to 3.5% of an interface mediator with a kinematic viscosity of from 10 cSt to 100 000 cSt at 25° C.,
and
C) optionally an additional skin contact layer.

According to certain embodiments of the invention, the TTS may comprise in addition to the active agent-containing self-adhesive layer structure attached thereto a larger active agent-free self-adhesive layer structure, e.g., an overlaying adhesive, for enhancing the adhesive properties of the overall transdermal therapeutic system. Said active agent-free self-adhesive layer structure comprises also a backing layer. In certain embodiments, this additional layer is beige colored. The area of said second active agent-free self-adhesive layer structure adds to the overall size of the TTS but does not add to the area of release. The pressure-sensitive adhesive compositions of the active agent-containing and the active agent-free self-adhesive layer structures may be the same or different. E.g., the active agent-free pressure-sensitive adhesive composition may comprise a pressure-sensitive adhesive polymer or polymer mixture selected from the group of polysiloxanes or polyisobutylenes.

A TTS according to the invention is normally located on a detachable protective layer (release liner) from which it is removed immediately before application to the surface of the patient's skin. A TTS protected this way may be stored in a blister pack or a side sealed bag.

Active Agent-Containing Self-Adhesive Layer Structure

In accordance with the invention, the active agent-containing self-adhesive layer structure comprises a backing layer, an active agent-containing dried biphasic layer and optionally an additional skin contact layer.

The size of the active agent-containing self-adhesive layer structure providing the area of release ranges from 1 cm² to 60 cm², and may be about 5 cm², about 10 cm², about 20 cm², about 30 cm², about 40 cm², or about 50 cm². The amount of rotigotine provided by the TTS per hour (mg/h) is proportional to the size of the area of release of a TTS and may be used to distinguish TTSs by the dosage strength.

The active agent-containing self-adhesive layer structure contains a therapeutically effective amount of a systemically active agent. In a preferred embodiment the systemically active agent is an amine functional drug, which has an octanol/water partitioning coefficient log P~2.8 at pH 7.4. In another preferred embodiment the amine functional drug has a pKa of 7.4 to 8.4. In an especially preferred embodiment the amine functional drug has an octanol/water partitioning coefficient log P~2.8 at pH 7.4 and a pKa of 7.4 to 8.4. The pKa value can be measured by standard methods. A particularly preferred method is potentiometric titration of aqueous drug solutions (without addition of organic cosolvents) at room temperature. The octanol/water partitioning coefficients (octan-1-ol/water partitioning coefficients) are determined at pH 7.4, 37° C. and an ionic strength of 0.15 in an appropriate buffer solution according to the method described by E. Miyamoto et al. (E. Miyamoto et al. "Physico-chemical Properties of Oxybutynin" Analyst (1994), 119, 1489-1492).

Particularly preferred amine functional drugs are dopamine D2 agonists, which are useful for example in the treatment of Parkinson's disease. Especially preferred dopamine D2 receptor agonists are aminotetraline compounds, such as 5,6,7,8-tetrahydro-6-[propyl-[2-(2-thienyl)ethyl] amino]-1-naphthalenol (INN: rotigotine).

Other examples for particularly preferred amine functional drugs are N-phenyl-N-[1-(2-phenylethyl)-4-piperidinyl]-propanamide (INN: fentanyl) which is useful in the treatment of pain and anticholinergic drugs exerting an antispasmodic effect on smooth muscles and inhibiting the muscarinic action of acetylcholin on smooth muscles. Examples of such anticholinergic drugs which are useful in the present invention are 4-diethylamino-2-butynyl phenylcyclohexylglycolate (INN: oxybutynine) and 2-[3-(diisopropylamino)-1-phenylpropyl]-4-(hydroxymethyl) phenyl isobutyrate (INN: fesoterodine). Oxybutynine and fesoterodine are useful in the treatment of urinary incontinence. It will be understood by a person skilled in the art that the amine functional drugs, such as rotigotine, fentanyl, oxybutynine and fesoterodine, may all exist in various isomeric forms. It has to be understood that in this case the amine functional drug may be any single isomer or a mixture of different isomers. If the amine functional group contains asymmetric carbon atoms, any single enantiomer or a mixture of enantiomers may be used. Rotigotine, fentanyl oxybutynine and fesoterodine all contain one asymmetric carbon atom. Hence, the S- or R-enantiomer or the racemate or any other enantiomer mixture of these compounds may be used as the amine functional drug.

According to certain embodiments of the invention, the systemically active agent is selected from the group consisting of rotigotine, fentanyl, oxybutynine, and fesoterodine, rotigotine is preferred.

According to certain embodiments of the invention, the active agent-containing self-adhesive layer structure may contain a therapeutically effective amount of rotigotine from 0.1 mg/cm$^2$ to 10.0 mg/cm$^2$, in particular from 0.1 mg/cm$^2$ to 5.0 mg/cm$^2$, or from 0.3 mg/cm$^2$ to 3.0 mg/cm$^2$.

Rotigotine exists in two different polymorphic states, Polymorphic Form I and Polymorphic Form II, which can be differentiated by their melting point, infrared (IR) spectroscopy, solid state nuclear magnetic resonance (SSNMR) or Raman spectroscopy as well as differential scanning calorimetry (DSC) and X-ray powder diffraction (XRD). The different physicochemical characteristics of the two polymorphic forms of rotigotine are for example described in WO 2009/068520. For the TTS according to one aspect of the invention, Polymorphic Form II is preferred.

Dried Biphasic Layer

The dried biphasic layer contains an outer and an inner phase. According to certain embodiments of the invention, the outer phase is hydrophobic and the inner phase is hydrophilic.

The active agent-containing biphasic layer may be coated at any area weight, but is preferably coated at an area weight of about 30 g/m$^2$ to about 400 g/m$^2$, or of about 30 g/m$^2$ to about 200 g/m$^2$, or of about 100 g/m$^2$ to about 200 g/m$^2$.

In a specific embodiment, the active agent-containing dried biphasic layer contains the active agent (e.g., rotigotine) in an amount of 1% to 30%, 10% to 26%, or 16% to 30%, or 16% to 26% of the dried biphasic layer.

According to a certain embodiment, the dried biphasic layer has an area weight of about 100 g/m$^2$ to about 200 g/m$^2$ and the active agent (e.g. rotigotine) is present in an amount of 16% to 26% of the dried biphasic layer.

The dried biphasic layer is obtained from a solvent-containing biphasic coating mixture after coating on a film and evaporating the solvents. The obtained layer (solvent-based layer) is to be distinguished from a biphasic layer obtained from a hot-melt coating mixture (hot melt-based layer). A biphasic layer obtained from a hot-melt coating mixture is characterized by different physico-chemical properties.

According to a certain embodiment of the invention, the active agent-containing dried biphasic layer is in direct contact with the skin.

According to a certain other embodiment of the invention, the active agent-containing self-adhesive layer structure comprises an additional skin contact layer which is also in the form of a dried biphasic layer and may be manufactured containing the active agent (e.g., rotigotine).

The dried biphasic layer of the TTS according to the invention may further comprise one or more anti-oxidants. Suitable anti-oxidants are sodium metabisulfite, ascorbyl palmitate, tocopherol and esters thereof, ascorbic acid, butylhydroxytoluene, butylhydroxyanisole or propyl gallate, preferably sodium metabisulfite, ascorbyl palmitate and tocopherol. The anti-oxidants may be conveniently present in an amount of from about 0.001% to about 0.5% of the dried biphasic layer.

The dried biphasic layer according to the invention may further comprise in addition to the above mentioned ingredients other various excipients or additives, for example from the group of solubilizers, fillers, tackifiers, substances which influence the barrier properties of the stratum corneum in the sense of increasing the active agent permeability, pH regulators, and preservatives. Suitable permeation enhancers may be selected from the group of fatty alcohols, fatty acids, fatty acid esters, fatty acid amides, glycerol or its fatty acid esters, N-methylpyrrolidone, terpenes such as limonene, [alpha]-pinene, [alpha]-terpineol, carvone, carveol, limonene oxide, pinene oxide, 1,8-eucalyptol and most preferably ascorbyl palmitate. In a preferred embodiment, the TTS according to the invention does not contain a penetration enhancer.

Outer Phase

In certain embodiments of the present invention, the outer phase of the active agent-containing dried biphasic layer has a composition comprising 75% to 100% of a polymer or polymer mixture. The polymer or polymer mixture in the outer phase may be (a) hydrophobic polymer(s).

In a certain embodiment of the invention, the composition of said outer phase is a pressure-sensitive adhesive composition.

In certain other embodiments of the invention, the polymer or polymer mixture in the outer phase is a/are pressure-sensitive adhesive polymer(s).

Pressure-sensitive adhesive polymers being suitable for solvent-containing coating mixtures exhibit a dynamic viscosity of above 150 Pa s at a temperature of 160° C.

In certain embodiments of the invention, the polymer or polymer mixture in the outer phase is a/are pressure-sensitive adhesive polymer(s) selected from the group of polysiloxanes, or polyisobutylenes, preferably the polymer or polymer mixture in the outer phase is a/are pressure-sensitive adhesive polysiloxane(s). Pressure-sensitive adhesive polysiloxanes provide for suitable tack for quick bonding to various skin types, including wet skin, suitable adhesive and cohesive qualities, long lasting adhesion to the skin of up to 7 days, a high degree of flexibility, a permeability to moisture, and compatibility to many actives and film-substrates. It is possible to provide them with sufficient amine resistance and therefore enhanced stability in the presence of amines. Such pressure-sensitive adhesive polymers are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The dimethiconol content contributes to the viscous component of the viscoelastic behavior, and impacts the wetting and the spreadability properties of the adhesive. The resin acts as a tackifying and reinforcing agent, and participates in the elastic component. The correct balance between dimethiconol and resin provides for the correct adhesive properties.

The adhesive strength of the pressure-sensitive polysiloxanes may be sufficient for the desired skin contact. In certain embodiments of the invention a plasticizer or a tackifying agent is incorporated into the formulation to improve the adhesive characteristics of the biphasic layer. It may be advantageous in an individual case to improve the tack by adding small amounts of tackifiers.

In certain embodiments of the invention, the polysiloxane(s) is/are amine-resistant. In further embodiments of the invention the polysiloxane(s) is/are amine-resistant being a product of the condensation reaction of silanol endblocked polydimethylsiloxane with a silica resin and the residual silanol functionality being capped with trimethylsiloxy groups.

Preferred pressure-sensitive adhesive polymers are supplied and used in solvents like heptane, ethyl acetate or other volatile silicone fluids. For the present invention pressure-sensitive adhesive mixtures of pressure-sensitive adhesive polysiloxane(s) in heptane or ethyl acetate are preferred. The solids content is usually between 60% and 80%.

The preferred pressure-sensitive adhesive mixtures of pressure-sensitive adhesive polysiloxane(s) in heptane in accordance with the invention are characterized by a solution viscosity at 25° C. and 60% solids content in heptane of more than 150 mPa s, or from about 200 mPa s to about 700 mPa s, in particular from about 350 mPa s to about 600 mPa s, more preferred from about 480 mPa s to about 550 mPa s, or most preferred of about 500 mPa s or alternatively from about 400 mPa s to about 480 mPa s, or most preferred of about 450 mPa s. These may also be characterized by a complex viscosity at 0.01 rad/s at 30° C. of less than about $1 \times 10^9$ Poise or from about $1 \times 10^5$ to about $9 \times 10^8$ Poise, or more preferred from about $1 \times 10^5$ to about $1 \times 10^7$ Poise, or most preferred about $5 \times 10^6$ Poise or alternatively more preferred from about $2 \times 10^7$ to about $9 \times 10^8$ Poise, or most preferred about $1 \times 10^8$ Poise.

The preferred pressure-sensitive adhesive mixtures of pressure-sensitive adhesive polysiloxane(s) in ethyl acetate in accordance with the invention are characterized by a solution viscosity at 25° C. and 60% solids content in ethyl acetate of more than 350 mPa s, or from about 400 mPa s to about 1500 mPa s, in particular from about 600 mPa s to about 1300 mPa s, more preferred from about 1100 mPa s to about 1300 mPa s, or most preferred of about 1200 mPa s or alternatively from about 700 mPa s to about 900 mPa s, or most preferred of about 800 mPa s. These may also be characterized by a complex viscosity at rad/s at 30° C. of less than about $1 \times 10\ 9$ Poise or from about $1 \times 10\ 5$ to about $9 \times 10\ 8$ Poise, or more preferred from about $1 \times 10^5$ to about $1 \times 10^7$ Poise, or most preferred about $5 \times 10^6$ Poise or alternatively more preferred from about $2 \times 10^7$ to about $9 \times 10^8$ Poise, or most preferred about $1 \times 10^8$ Poise.

According to a certain embodiment, a pressure-sensitive adhesive mixture of a pressure-sensitive adhesive polysiloxane in heptane characterized by a solution viscosity at and about 60% solids content in heptane of 500 mPa s and a pressure-sensitive adhesive polysiloxane in heptane characterized by a solution viscosity at 25° C. and about 60% solids content in heptane of 450 mPa s is preferred.

According to a certain other embodiment, a pressure-sensitive adhesive mixture of a pressure-sensitive adhesive polysiloxane in ethyl acetate characterized by a solution viscosity at 25° C. and about 60% solids content in ethyl acetate of 1200 mPa s and a pressure-sensitive adhesive polysiloxane in ethyl acetate characterized by a solution viscosity at 25° C. and about 60% solids content in ethyl acetate of 800 mPa s is preferred.

Suitable pressure-sensitive adhesive polysiloxanes may be obtained from DOW CORNING® BIO-PSA Standard Silicone Adhesives. Preferred pressure-sensitive adhesive mixtures of pressure-sensitive adhesive polysiloxane(s) in heptane are the BIO-PSA 7-4301 and BIO-PSA 7-4201 Silicone Adhesives, and in ethyl acetate the BIO-PSA 7-4302 and BIO-PSA 7-4202 Silicone Adhesives. According to certain embodiments of the invention, a mixture of BIO-PSA 7-4301 and BIO-PSA 7-4201 is preferred and according to certain other embodiments a mixture of BIO-PSA 7-4302 and BIO-PSA 7-4202 is preferred. According to certain embodiments the preferred mixtures provide a 50:50 ratio, according to certain other embodiments the mixtures provide a 60:40, or 70:30 ratio. A higher amount of BIO-PSA 7-4301, or BIO-PSA 7-4302, respectively, is preferred for a biphasic layer which provides the skin contact layer.

According to a certain embodiment of the invention, the TTS comprises a mixture of BIO-PSA 7-4301 and BIO-PSA 7-4201 in a ratio of 30:70 in the outer phase of the rotigotine-containing biphasic layer and a mixture of BIO-PSA 7-4301 and BIO-PSA 7-4201 in a ratio of 70:30 in the outer phase of the additional skin contact layer.

BIO-PSA 7-4301 has a solution viscosity at 25° C. and about 60% solids content in heptane of 500 mPa s and a complex viscosity at 0.01 rad/s at 30° C. of $5 \times 10\ 6$ Poise. BIO-PSA 7-4201 has a solution viscosity at 25° C. and about 60% solids content in heptane of 450 mPa s and a complex viscosity at 0.01 rad/s at 30° C. of $1 \times 10\ 8$ Poise. BIO-PSA 7-4302 has a solution viscosity at 25° C. and about 60% solids content in ethyl acetate of 1200 mPa s and a complex viscosity at 0.01 rad/s at 30° C. of $5 \times 10\ 6$ Poise. BIO-PSA 7-4202 has a solution viscosity at 25° C. and about 60% solids content in heptane of 800 mPa s and a complex viscosity at 0.01 rad/s at 30° C. of $1 \times 10^8$ Poise.

Inner Phase

According to the invention, the inner phase comprises the active agent. According to one aspect of the invention, the inner phase also comprises a hydrophilic agent forming a solid solution with the active agent.

In order to form a solid solution with the active agent a hydrophilic agent may be present in the inner phase. In a certain embodiment of the present invention this hydrophilic agent is a hydrophilic polymer or polymer mixture. The hydrophilic polymer(s) is/are selected from the group consisting of polyvinylpyrrolidones having a K-Value of from 10 to 200,
copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
acrylic polymers,
modified celluloses.

In a further embodiment of the present invention, the hydrophilic polymer(s) is/are selected from the group consisting of:

polyvinylpyrrolidones having a K-Value of from 10 to 200,
copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
copolymers of dimethylaminoethyl methacrylate, butyl methacrylate and methyl methacrylate,
copolymers of methacrylic acid and methyl methacrylate,
hydroxypropyl methylcellulose, hydroxypropyl methylcellulose acetate succinate.

In accordance with a certain specific embodiment of the invention the polymer in the inner phase comprises polyvinylpyrrolidone(s), in particular having a K-Value of from to 200, or 90.

According to the invention, the inner phase forms dispersed deposits in the outer phase of the biphasic layer. According to a specific embodiment of the invention, the maximum droplet size of the dispersed deposits is from 5 μm to 25 μm.

Interface Mediator

According to the invention the interface mediator is present in the biphasic layer in an amount of 0.1% to 3.5%.

Useful concentrations of the interface mediator are in particular to 3%, or 0.1% to 2%, or 0.1% to 1.5%.

According to the present invention the interface mediator has a kinematic viscosity of from about 10 cSt to about 100 000 cSt at 25° C., preferably from about 100 cSt to about 100 000 cSt, or about 200 cSt to about 100 000 cSt, or about 500 cSt to about 100 000 cSt, or about 800 cSt to about 100 000 cSt, or about 1 000 cSt to about 100 000 cSt, or about 10 000 cSt to about 100 000 cSt at 25° C., or a kinematic viscosity of from about 100 cSt to about 30 000 cSt, or about 200 cSt to about 30 000 cSt, or about 500 cSt to about 000 cSt, or about 800 cSt to about 30 000 cSt, or about 1 000 cSt to about 30 000 cSt, or about 10 000 cSt to about 30 000 cSt at 25° C., or a kinematic viscosity of from about 100 cSt to about 15 000 cSt, 200 cSt to about 15 000 cSt, or about 500 cSt to about 15 000 cSt, or about 800 cSt to about 15 000 cSt, or about 1 000 cSt to about 15 000 cSt, or about 10 000 cSt to about 15 000 cSt at 25° C.

The methods of measuring the kinematic viscosity are known, follow standardized procedures and provide interchangeable results.

As known for the skilled person, the viscosimeters are calibrated with certified viscosity reference standards. Certified viscosity reference standards are certified by a laboratory that has been shown to meet the requirements of ISO 17025 (initially issued by the International Organization for Standardization in 1999, reviewed in 2005) by independent assessment. Viscosity standards shall be traceable to master viscometer procedures described in standard method ASTM D2162 (originally approved in 1963, ASTM D2162-13 revised in 2013), the internationally recognized method for viscosity reference standards under ISO/IEC 17025 guidelines.

The standard test method for the determination of the kinematic viscosity is ASTM D445 (originally approved in 1937, ASTM D445-12 revised in 2012) which corresponds to ISO 3104. The range of kinematic viscosities covered by this test method is from 0.2 to 300 000 cSt. The specification of ASTM D445, which refers to the standard calibration method ASTM D2162, lists about 20 different capillary viscometers, e.g., Ubbelohde and Cannon type viscometers, useful for determining the kinematic viscosity according to the standard test method. However, as stated in ASTM D445, it is not intended to restrict the test method to the use of only those viscometers listed in the specification. The kinematic viscosity according to the present invention can thus be determined by any calibrated viscometer covering the desired kinematic viscosity range. Ubbelohde viscometers, for example, cover a kinematic viscosity range of from about 0.3 cSt to about 100 000 cSt (see, e.g., ASTM D445-12) and are useful viscometers for the determination of the kinematic viscosity of from about 10 cSt to about 100 000 cSt at 25° C.

The kinematic viscosity according to the invention may, e.g., be determined by the standard test method ASTM D445, e.g., ASTM D445-12, e.g., using Ubbelohde viscometers calibrated with the standard method ASTM D2162, e.g., ASTM D2162-13.

The kinematic viscosity according to the present invention can likewise be determined by measuring the dynamic viscosity of the interface mediator. The kinematic viscosity is the ratio of the dynamic viscosity to the density of the substance. Suitable viscometers for the determination of the dynamic viscosity are rotational viscometers such as Brookfield cup/spindle viscometers and cone/plate viscometers. Standard test methods that are suitable for determining the dynamic viscosity are ASTM D1084 (e.g., ASTM D1084-08) and ASTM D4287 (e.g., ASTM D4287-00). The methods provide interchangeable results if the viscosimeters are calibrated with certified viscosity reference standards.

A possible practicable method is that the standard test method ASTM D445 (e.g, ASTM D445-12) is used for measuring kinematic viscosities of less than 1 000 cSt at 25° C., e.g., for measuring a kinematic viscosity of about 20 cSt, about 100 cSt or about 350 cSt, and that one of the standard test methods for measuring the dynamic viscosity, ASTM D1084 (e.g., ASTM D1084-08) or ASTM D4287 (e.g., ASTM D4287-00), is used for determining kinematic viscosities of about 1 000 cSt or more at 25° C., e.g. for determining a kinematic viscosity of about 1 000 cSt, or about 12 500 cSt as described in Dow Corning's Corporate Test Mehods CTM 0004 and CTM 0050. For determining kinematic viscosities of about 1 000 cSt or more at 25° C., e.g., for determining a kinematic viscosity range of from about 1 000 cSt to about 100 000 cSt at 25° C., the standard test method ASTM D1084 is practicable.

According to one aspect of the invention, the interface mediator is used to reduce the maximum droplet size of the dispersed deposits of the inner phase in the outer phase in a dried biphasic layer of a transdermal therapeutic system as described above. Without wishing to be bound to any theory it is believed that this effect is achieved by filling cavities at the interface between the dispersed inner phase and the outer phased and thereby enhancing the compatibility of the two separate phases and promoting a maximum separation/dispersion of the inner phase in the outer phase.

According to certain embodiments of the invention, the interface mediator is hydrophobic when the outer phase is hydrophobic.

In accordance with certain embodiments of the invention, the interface mediator is a silicone oil, preferably with a kinematic viscosity of about 10 cSt to about 100 000 cSt, or about 100 cSt to about 30 000 cSt, or about 10 000 cSt to about 15 000 cSt (e.g., DOW CORNING® Medical Fluid).

Preferably, the silicone oil has a kinematic viscosity of from about 100 cSt to about 100 000 cSt, or about 200 cSt to about 100 000 cSt, or about 500 cSt to about 100 000 cSt, or about 800 cSt to about 100 000 cSt, or about 1 000 cSt to about 100 000 cSt, or about 10 000 cSt to about 100 000 cSt at 25° C., or a kinematic viscosity of from about 100 cSt to about 30 000 cSt, or about 200 cSt to about 30 000 cSt, or about 500 cSt to about 000 cSt, or about 800 cSt to about 30 000 cSt, or about 1 000 cSt to about 30 000 cSt, or about 10 000 cSt to about 30 000 cSt at 25° C., or a kinematic viscosity of from about 100 cSt to about 15 000 cSt, 200 cSt to about 15 000 cSt, or about 500 cSt to about 15 000 cSt, or about 800 cSt to about 15 000 cSt, or about 1 000 cSt to about 15 000 cSt, or about 10 000 cSt to about 15 000 cSt at 25° C.

According to one aspect of the invention, a silicone oil is used as interface mediator in a transdermal therapeutic system with an active agent-containing dried biphasic layer having a hydrophilic inner phase and a hydrophobic outer phase for controlling the maximum droplet size of the inner phase of said dried biphasic layer, in particular in a transdermal therapeutic system wherein the active agent is rotigotine base and is present in the dried biphasic layer in an amount of 16% to 26% of the dried biphasic layer.

Skin Contact Layer

The TTS in accordance with the invention may comprise an additional skin contact layer which is an adhesive layer.

According to a certain embodiment, the additional skin contact layer has a pressure-sensitive adhesive composition comprising pressure-sensitive polymers selected from polysiloxanes, or polyisobutylenes. A pressure-sensitive adhesive composition comprising pressure-sensitive adhesive polysiloxane(s) is preferred according to a certain embodiment of the invention.

The additional skin contact layer may be manufactured active agent-free or active agent-containing.

Method of Manufacture

According to one aspect, the invention relates to a method of manufacture of an active agent-containing dried biphasic layer comprising the steps of:
(1) preparing a biphasic coating mixture having an inner phase dispersed in an outer phase:
   (a) the inner phase comprising the active agent,
   (b) the outer phase comprising a polymer or polymer mixture, wherein the biphasic coating mixture comprises solvents in sufficient amounts to provide for a viscosity of the coating mixture suitable for coating,
(2) adding to said biphasic coating mixture an interface mediator, and mixing said coating mixture to provide a suitable dispersion of the inner phase in the outer phase,
(3) coating said coating mixture on a film to provide a layer of said solvent-containing mixture,
(4) evaporating said solvents to provide a dried layer with a coating weight to provide said active agent-containing dried biphasic layer with the desired area weight,
(5) optionally laminating two or more of said dried layers to provide said active agent-containing dried biphasic layer with the desired area weight.

in particular to a dried biphasic layer obtainable by said process.

According to one further aspect, the invention relates to a method of manufacture of a transdermal therapeutic system comprising an active agent-containing dried biphasic layer, comprising the steps of:
(1) preparing a biphasic coating mixture having an inner phase dispersed in an outer phase:
   (a) the inner phase comprising the active agent,
   (b) the outer phase comprising a polymer or polymer mixture, wherein the biphasic coating mixture comprises solvents in sufficient amounts to provide for a viscosity of the coating mixture suitable for coating,
(2) adding to said biphasic coating mixture an interface mediator, and mixing said coating mixture to provide a suitable dispersion of the inner phase in the outer phase,
(3) coating said coating mixture on a film to provide a layer of said solvent-containing mixture,
(4) evaporating said solvents to provide a dried layer with a coating weight to provide an active agent-containing dried biphasic layer with the desired area weight,
(5) optionally laminating two or more of said dried layers to provide an active agent-containing dried biphasic layer with the desired area weight,
(6) laminating said active agent-containing dried biphasic layer to a backing layer,
(7) optionally laminating said active agent-containing biphasic layer to an additional skin contact layer.

According to a certain embodiment of the invention, a pressure-sensitive adhesive mixture of pressure-sensitive adhesive polysiloxanes in heptane or ethyl acetate is used for the production of the biphasic layer and optionally the additional skin contact layer.

Useful solvents for dissolving the polymer mixture comprising at least two hydrophilic polymers are alcohols (e.g., ethanol), acetone and methyl ethyl ketone, ethanol is preferred. The composition comprising 75% to 100% of a polymer or a polymer mixture may be dissolved in heptanes, hexanes, toluene, or ethyl acetate, preferably in heptane or ethyl acetate.

According to a certain embodiment of the invention, the active agent-containing dried biphasic layer is laminated to an additional skin contact layer and wherein the preparation of the skin contact layer comprises the steps of:
(1) providing an adhesive coating mixture,
(2) coating said adhesive coating mixture on a film in an amount to provide the desired area weight,
(3) drying said coated adhesive composition to provide a skin contact layer with the desired area weight.

Method of Treatment/Medical Use

According to one aspect, the transdermal therapeutic system in accordance with one specific aspect of the invention containing rotigotine as active agent and as described above in detail is for use in a method of treatment, in particular for use in a method of treating patients suffering from Parkinson's disease, Parkinson's plus syndrome, depression, anxiety, ADHS, fibromyalgia, the restless-legs syndrome and for use in the treatment or prevention of dopaminergic neuron loss or the treatment or prevention of cognitive disorders, dementia or lewy body disease.

The method comprises in particular the application of the TTS for 7 days on the skin of a human patient. According to other methods in accordance with the invention the TTS can be applied for at least 1 day, or 3 days, or 4 days on the skin of a human patient. A 7 day-application is preferred.

The TTS according to the invention is in particular for use in a method of treatment by applying a transdermal therapeutic system for 7 days on the skin of a human patient. According to other aspects of the invention, the TTS is for use in a method of treatment by applying a transdermal therapeutic system for at least 1 day, 3 days, or 4 days on the skin of a human patient. A 7 day-application is preferred.

According to certain embodiments of the invention, therapeutically effective amounts of the active agent (e.g., rotigotine) are provided for 1 to 7 days by said transdermal therapeutic system during an administration period of 1 to 7 days.

A multi-day TTS according to the invention has the advantage of allowing for a reduced application frequency compared to daily applied transdermal therapeutic systems. This is particularly advantageous for patients suffering from severe dopaminergic disorders, like Parkinson's disease, as these patients often experience motor disabilities which make the frequent handling and administration of transdermal therapeutic systems difficult. At the same time, the number of skin application sites to be treated with transdermal therapeutic systems during a long-term medication is reduced. A prolongation of the medication interval, e.g., from 1 day to at least 3 or even at least 7 days minimizes the potential risk of skin lesions associated with repeated TTS stripping from the patients' skin at skin application sites selected for repeated TTS administration. E.g., for the once-daily TTS NEUPRO® 14 different skin application sites are necessary for repeated TTS application to avoid skin irritation, whereas with a once-weakly TTS only 3 skin application sites are necessary. In addition, the influence of inter- and intra-individually differing lag-times on the absorption of the active agent (e.g., rotigotine), which may be associated with the daily replacement of active agent-containing transdermal therapeutic systems in the case of low skin permeability and which may cause therapeutically unwanted fluctuations of the plasma levels of the active agent (e.g., rotigotine), can be eliminated by the multi-day TTS of the present invention. Finally, the replacement of a daily TTS administration by one single administration for several days, for example by an administration once or twice weekly, contributes to the reduction of the costs of the respective medication by saving material and production time.

According to certain embodiments of the invention, therapeutically effective amounts of the active agent (e.g., rotigotine) are provided for 3 days by the transdermal therapeutic system according to the invention during an administration period of 3 days, preferably for 4 days during an administration period of 4 days, or for 7 days during an administration period of 7 days.

EXAMPLES

The present invention will now be more fully described with reference to the accompanying examples. It should be understood, however, that the following description is illustrative only and should not be taken in any way as a restriction of the invention.

Example 1

Preparation of the Biphasic Coating Mixture:

At first, an ethanolic polyvinylpyrrolidone (PVP) solution containing 12.8% by weight of KOLLIDON® 90F was manufactured.

The composition of the PVP solution is summarized in Table 1 below.

TABLE 1

| Excipients | Quantity [g] | Quantity [%] |
|---|---|---|
| Ascorbyl palmitate | 0.25 | 0.11 |
| Alpha tocopherol | 0.62 | 0.28 |
| Sodium metabisulfite solution 10% (w/w) | 0.226 | 0.006 |
| Polyvinylpyrrolidone (KOLLIDON ® 90F) | 50.00 | 12.83 |
| Ethanol | 338.6 | 86.89 |
| Total amount | 389.695 | 100.00 |

50.00 g PVP (KOLLIDON® 90F), 0.62 g DL-α-Tocopherol, 0.25 g ascorbyl palmitate and 0.226 g of an aqueous sodium metabisulfite solution (10% by weight) were mixed with 338.6 g anhydrous ethanol to obtain a clear solution.

The composition of the rotigotine-containing biphasic coating mixture is summarized in Table 2 below.

TABLE 2

| Excipients | Quantity [g] | Quantity [%] |
|---|---|---|
| PVP solution | 19.00 | 19.79 |
| Rotigotine | 5.50 | 5.73 |
| BIO-PSA 7-4201 (73.5%) | 36.00 | 37.50 |
| BIO-PSA 7-4301 (74.6%) | 35.50 | 36.98 |
| Total amount | 96.00 | 100.00 |

19.0 g of the stabilized PVP solution and 5.50 g rotigotine of polymorphic form II were mixed and heated to 60° C. for 90 min until a clear solution was obtained.

36.00 g silicone adhesive BIO-PSA 7-4201 (73.5% by weight in n-heptane) and g silicone adhesive BIO-PSA 7-4301 (74.6% by weight in n-heptane) were added to the obtained solution of rotigotine, PVP and antioxidants and stirred for 40 min.

At the end of the manufacture of the 100 g rotigotine-containing biphasic coating mixture, it was split into five samples of approximately 20 g. One sample was stored at room temperature without further treatment (Example 1A).

In order to investigate the influence of an interface mediator on the droplet size distribution in the biphasic coating mixture silicone oils with different viscosities (100 cSt, 350 cSt, 1000 cSt and 12500 cSt) were added under stirring at a concentration of 1% by weight to the other four samples resulting in Examples 1B-E.

The composition of the mixtures is summarized in Table 3 below.

TABLE 3

| | 1B (100 cSt) | 1C (350 cSt) | 1D (1 000 cSt) | 1E (12 500 cSt) |
|---|---|---|---|---|
| Drug containing mass (1A) | 20.0 g | 20.0 g | 20.0 g | 20.0 g |
| Silicone oil | 0.2 g | 0.2 g | 0.2 g | 0.2 g |
| Total amount | 20.2 g | 20.2 g | 20.2 g | 20.2 g |

Microscopic pictures were taken of the biphasic coating mixture after preparation. FIG. 1 shows a microscopic picture of the biphasic coating mixture of Example 1A. FIGS. 2-5 show microscopic pictures of the biphasic coating mixture of Examples 1 B-1E.

During the microscopic investigation the droplet size (diameter) was determined. The maximum droplet sizes in the rotigotine-containing biphasic coating mixture are summarized in Table 4 below.

TABLE 4

| Mixture | 1A | 1B | 1C | 1D | 1E |
|---|---|---|---|---|---|
| Maximum droplet size | 28 μm | 20 μm | 17 μm | 15 μm | 13 μm |

Example 2

The composition of the rotigotine-containing biphasic coating mixture (Example 2A) is summarized in Table 5 below.

TABLE 5

| | Example 2A | |
|---|---|---|
| Exipients | Composition solid [%] | Composition solution [%] |
| Ethanol | — | 14.902 |
| Ethanol dilution | — | 12.078 |
| Polyvinylpyrrolidone (KOLLIDON ® 90 F) | 8.00 | 4.401 |
| Sodium metabisulfite solution 10% (w/w) | 0.0036 | 0.020 |
| Ascorbyl palmitate | 0.0401 | 0.0220 |
| All-rac-Tocopherol | 0.0994 | 0.0547 |
| Rotigotine | 18.00 | 9.902 |
| BIO-PSA 7-4301 (71.5%) | 36.93 | 28.413 |
| BIO-PSA 7-4201 (71.5%) | 36.93 | 28.413 |
| n-Heptane | — | 1.796 |
| Total amount | 100.0 | 100.0 |

The composition of the rotigotine-containing biphasic coating mixture with 1% silicone oil (Example 2B) is summarized in Table 6 below.

TABLE 6

|  | Example 2B | |
|---|---|---|
| Excipients | Composition solid [%] | Composition solution [%] |
| Ethanol | — | 26.98 |
| Polyvinylpyrrolidone (KOLLIDON ® 90 F) | 8.00 | 4.40 |
| Sodium metabisulfite solution 10% (w/w) | 0.0036 | 0.020 |
| Ascorbyl palmitate | 0.0401 | 0.022 |
| All-rac-Tocopherol | 0.0994 | 0.055 |
| Rotigotine | 18.00 | 9.90 |
| BIO-PSA 7-4301 (71.5%) | 36.02 | 27.71 |
| BIO-PSA 7-4201 (71.5%) | 36.02 | 27.71 |
| Silicone oil (12500 cSt) | 1.817 | 1.000 |
| n-Heptane | — | 2.19 |
| Total amount | 100.0 | 100.0 |

Preparation of the Rotigotine-Containing Biphasic Coating Mixture (Step 1):

8.80 g polyvinylpyrrolidone (PVP, KOLLIDON® 90F), 0.109 g DL-α-Tocopherol, 0.044 g ascorbyl palmitate and 0.040 g of an aqueous sodium metabisulfite solution (10% by weight) were mixed with 53.96 g anhydrous ethanol to obtain a clear solution (2000 rpm, propeller stirrer).

19.8 g rotigotine of polymorphic Form II were added while stirring at 600 rpm and heated to 60° C. for 60 min.

55.42 g silicone adhesive 7-4201 (71.5% by weight in n-heptane), 55.42 g silicone adhesive 7-4301 (71.5% by weight in n-heptane) and, in case of Example 2B, 2.00 g silicone oil (12500 cSt) were added to the obtained solution of rotigotine, PVP and antioxidants and stirred at 1200 rpm for 5 min (turbine stirrer).

Preparation of the Transdermal Therapeutic System (TTS) (Step 2):

The mixture obtained in step 1 was coated onto two sheets of a suitable polyester release liner (e.g., SCOTCHPAK™ 9755) to obtain two rotigotine-containing biphasic layers each having a coating weight of 75 g/m². The coated release liner sheets were placed in a drying oven and dried at 50° C. for about 30 min and then at 115° C. for about 10 min. The first dried rotigotine-containing layer was laminated with (1) a polyester-type backing foil and (2) the second rotigotine-containing layer after removal of the release liner from the surface of the first rotigotine-containing layer to provide the rotigotine-containing self-adhesive layer structure having an area weight of 150 g/m². Finally, individual systems (TTS) having a size of 10 cm² were punched out of the complete laminate and sealed into pouches.

Figure 6:
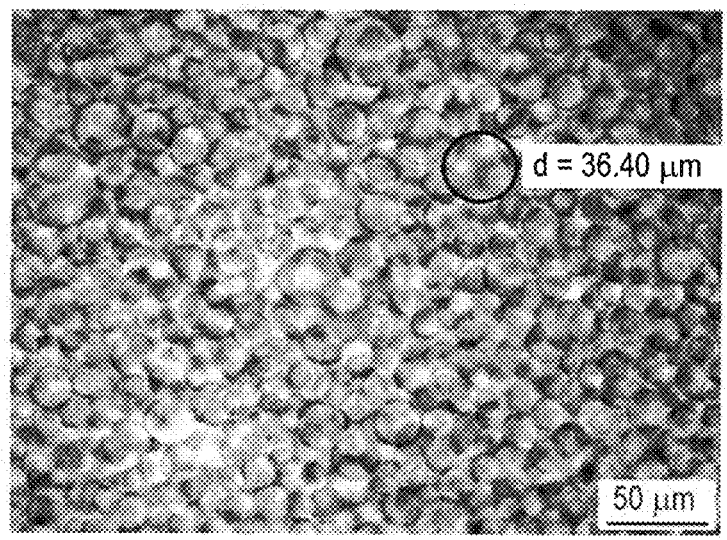
FIG. 6 depicts the rotigotine-containing biphasic coating mixture of Example 2A.
Figure 7:
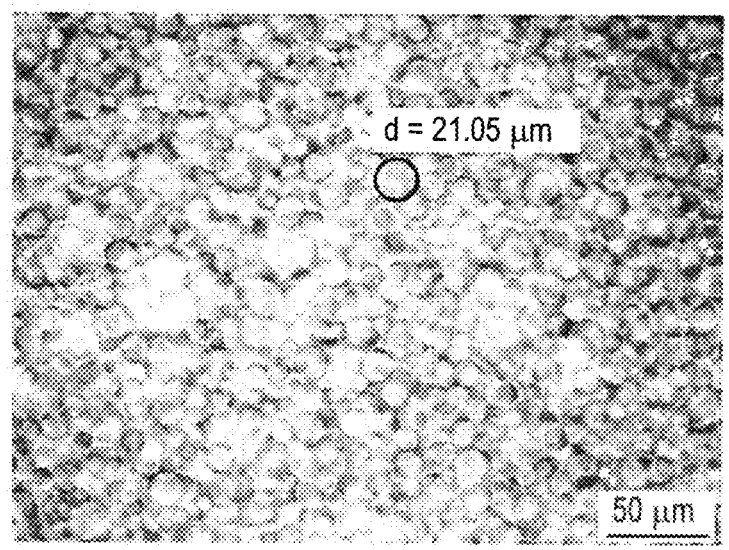
FIG. 7 depicts the rotigotine-containing biphasic coating mixture of Example 2B with 1% silicone oil (DOW CORNING® Medical Fluid 12500 cSt).

Microscopic pictures of the rotigotine-containing biphasic coating mixture were taken using a Nikon Microscope with a Leica camera. FIGS. 6 and 7 show microscopic pictures of the rotigotine-containing biphasic coating mixture of Example 2A and 2B.

During the microscopic investigation the droplet size (diameter) was determined. The maximum droplet sizes found in the respective dried biphasic layers in FIGS. 6 and 7 are listed in Table 7 below.

TABLE 7

|  | Mixture | |
|---|---|---|
|  | Example 2A without silicone oil | Example 2B with 1% silicone oil |
| Maximum droplet size | 36 μm | 21 μm |

The invention relates in particular to the following further items:

1. Transdermal therapeutic system for the transdermal administration of a systemically active agent comprising a self-adhesive layer structure,
   comprising
   A) a backing layer, and
   B) a dried biphasic layer, the dried biphasic layer having
      a) an outer phase having a composition comprising 75% to 100% of a polymer or polymer mixture, and
      b) an inner phase having a composition comprising at least one active agent,
      wherein the inner phase forms dispersed deposits in the outer phase,
      and
      c) 0.1% to 3.5% of an interface mediator other than silicone oil with a kinematic viscosity of from 10 cSt to 100 000 cSt at 25° C.,
   and
   C) optionally an additional skin contact layer.

2. Transdermal therapeutic system in accordance with item 1 comprising 0.1% to 3% of an interface mediator.

3. Transdermal therapeutic system in accordance with item for 2 comprising 0.1% to 2% of an interface mediator.

4. Transdermal therapeutic system in accordance with any one of items 1 to 3 comprising to 1.5% of an interface mediator.

5. Transdermal therapeutic system in accordance with any one of items 1 to 4, wherein the outer phase is hydrophobic and the inner phase is hydrophilic.

6. Transdermal therapeutic system in accordance with any one of items 1 to 5, wherein said outer phase is a pressure-sensitive adhesive composition.

7. Transdermal therapeutic system in accordance with any one of items 1 to 6, wherein said polymer or polymer mixture in the outer phase is a/are hydrophobic polymer(s).

8. Transdermal therapeutic system in accordance with item 7, wherein the hydrophobic polymer or polymer mixture in the outer phase is a/are pressure-sensitive adhesives polymer(s) selected from the group of polysiloxanes, or polyisobutylenes.

9. Transdermal therapeutic system in accordance with item 8, wherein the hydrophobic polymer or polymer mixture is a/are pressure-sensitive adhesive polysiloxane(s).

10. Transdermal therapeutic system in accordance with item 9, wherein the polysiloxane(s) is/are amine-resistant.

11. Transdermal therapeutic system in accordance with item 9, wherein the polysiloxane(s) is/are amine-resistant being a product of the condensation reaction of silanol endblocked polydimethylsiloxane with a silica resin and the residual silanol functionality being capped with trimethylsiloxy groups.

12. Transdermal therapeutic system in accordance with any one of items 1 to 11, wherein for the production of the dried biphasic layer and optionally the additional skin contact layer a pressure-sensitive adhesive mixture of pressure-sensitive adhesive polysiloxane(s) in heptane is used.

13. Transdermal therapeutic system in accordance with item 12, wherein the pressure-sensitive adhesive mixture is characterized by a solution viscosity at 25° C. and 60% solids content in heptane of more than 150 mPa s.

14. Transdermal therapeutic system in accordance with item 12, wherein the pressure-sensitive adhesive mixture is characterized by a solution viscosity at 25° C. and 60% solids content in heptane of from about 200 mPa s to about 700 mPa s.

15. Transdermal therapeutic system in accordance with item 12, wherein the pressure-sensitive adhesive mixture is characterized by a solution viscosity at 25° C. and 60% solids content in heptane of from about 350 mPa s to about 600 mPa s.

16. Transdermal therapeutic system in accordance with any one of items 1 to 15, wherein for the production of the dried biphasic layer and optionally the additional skin contact layer a pressure-sensitive adhesive mixture of pressure-sensitive adhesive polysiloxane(s) in ethyl acetate is used.

17. Transdermal therapeutic system in accordance with item 16, wherein the pressure-sensitive adhesive mixture is characterized by a solution viscosity at 25° C. and 60% solids content in ethyl acetate of more than 350 mPa s.

18. Transdermal therapeutic system in accordance with item 16, wherein the pressure-sensitive adhesive mixture is characterized by a solution viscosity at 25° C. and 60% solids content in ethyl acetate of from about 400 mPa s to about 1500 mPa s.

19. Transdermal therapeutic system in accordance with item 16, wherein the pressure-sensitive adhesive mixture is characterized by a solution viscosity at 25° C. and 60% solids content in ethyl acetate of from about 600 mPa s to about 1300 mPa s.

20. Transdermal therapeutic system in accordance with any one of items 9 to 19, wherein the pressure-sensitive adhesive polysiloxane(s) is/are characterized by a complex viscosity at 0.01 rad/s at 30° C. of less than $1 \times 10^9$ Poise.

21. Transdermal therapeutic system in accordance with any one of items 9 to 19, wherein the pressure-sensitive adhesive polysiloxane(s) is/are characterized by a complex viscosity at 0.01 rad/s at 30° C. of from about $1 \times 10^5$ to about $9 \times 10^9$ Poise.

22. Transdermal therapeutic system in accordance with any one of items 1 to 11, wherein for the production of the dried biphasic layer and optionally the additional skin contact layer a pressure-sensitive adhesive mixture of a pressure-sensitive adhesive polysiloxane in heptane characterized by a solution viscosity at 25° C. and about 60% solids content in heptane of 500 mPa s and a pressure-sensitive adhesive polysiloxane in heptane characterized by a solution viscosity at 25° C. and about 60% solids content in heptane of 450 mPa s is used.

23. Transdermal therapeutic system in accordance with any one of items 1 to 11, wherein for the production of the dried biphasic layer and optionally the additional skin contact layer a pressure-sensitive adhesive mixture of a pressure-sensitive adhesive polysiloxane in ethyl acetate characterized by a solution viscosity at 25° C. and about 60% solids content in ethyl acetate of 1200 mPa s and a pressure-sensitive adhesive polysiloxane in ethyl acetate characterized by a solution viscosity at 25° C. and about 60% solids content in ethyl acetate of 800 mPa s is used.

24. Transdermal therapeutic system in accordance with any one of items 1 to 23, wherein the inner phase comprises a hydrophilic agent and the systemically active agent forms a solid solution with the hydrophilic agent.

25. Transdermal therapeutic system in accordance with item 24, wherein the hydrophilic agent in the inner phase is a hydrophilic polymer or polymer mixture.

26. Transdermal therapeutic system in accordance with any one of items 24 and 25, wherein the hydrophilic polymer or polymer mixture in the inner phase is selected from the group consisting of
polyvinylpyrrolidones having a K-Value of from 10 to 200,
copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
acrylic polymers,
modified celluloses.

27. Transdermal therapeutic system in accordance with any one of items 24 and 25, wherein the hydrophilic polymer or polymer mixture in the inner phase is selected from the group consisting of
polyvinylpyrrolidones having a K-Value from 10 to 200,
copolymers of vinyl caprolactam, vinylacetate and ethylene glycol,
copolymers of vinylpyrrolidone and vinylacetate,
copolymers of ethylene and vinylacetate,
polyethylene glycols,
polypropylene glycols,
copolymers of dimethylaminoethyl methacrylate, butyl methacrylate and methyl methacrylate,
copolymers of methacrylic acid and methyl methacrylat,
hydroxypropyl methylcellulose, hydroxypropyl methylcellulose acetate succinate.

28. Transdermal therapeutic system in accordance with any one of items 25 to 27, wherein the hydrophilic polymer or polymer mixture in the inner phase is a/are polyvinylpyrrolidone(s).

29. Transdermal therapeutic system in accordance with item 27, wherein the polyvinylpyrrolidone(s) in the inner phase is a/are polyvinylpyrrolidone(s) having a K-Value of from 10 to 200, in particular 90.

30. Transdermal therapeutic system in accordance with any one of items 1 to 29, wherein the outer phase is hydrophobic and the interface mediator is hydrophobic.

31. Transdermal therapeutic system in accordance with item 30, wherein the interface mediator exhibits a kinematic viscosity of about 100 cSt to about 30 000 cSt.

32. Transdermal therapeutic system in accordance with item 30 or 31, wherein the interface meditor exhibits a kinematic viscosity of about 10 000 cSt to about 15 000 cSt.

33. Transdermal therapeutic system in accordance with any one of items 1 to 32, wherein the active agent is selected from the group of rotigotine, fentanyl, oxybutynine, and fesoterodine.

34. Transdermal therapeutic system in accordance with any one of items 1 to 33, wherein the active agent is rotigotine base or a pharmaceutically acceptable salt thereof.

35. Transdermal therapeutic system in accordance with item 34, wherein the transdermal therapeutic system contains 0.1 mg/cm$^2$ to 10.0 mg/cm$^2$ of rotigotine base in said self-adhesive layer structure.

36. Transdermal therapeutic system in accordance with any one of items 34 to 35, wherein the transdermal therapeutic system contains 0.1 mg/cm$^2$ to 5.0 mg/cm$^2$ of rotigotine base in said self-adhesive layer structure.

37. Transdermal therapeutic system in accordance with any one of items 35 to 36, wherein the transdermal therapeutic system contains 0.3 mg/cm$^2$ to 3.0 mg/cm$^2$ of rotigotine base in said self-adhesive layer structure.

38. Transdermal therapeutic system in accordance with any one of items 35 to 37, wherein the transdermal therapeutic system contains 0.3 mg/cm$^2$ to 1.0 mg/cm$^2$ of rotigotine base in said self-adhesive layer structure.

39. Transdermal therapeutic system in accordance with items 35 to 37, wherein the transdermal therapeutic system contains 1.0 mg/cm$^2$ to 1.5 mg/cm$^2$ of rotigotine base in said self-adhesive layer structure.

40. Transdermal therapeutic system in accordance with item 35, wherein the transdermal therapeutic system contains 1.5 mg/cm$^2$ to 5.0 mg/cm$^2$ of rotigotine base in said self-adhesive layer structure.

41. Transdermal therapeutic system in accordance with any one of items 35 to 40, wherein the transdermal therapeutic system contains 2.0 mg/cm$^2$ to 4.0 mg/cm$^2$, preferably 2.0 mg/cm$^2$ to 3.0 mg/cm$^2$ of rotigotine base in said self-adhesive layer structure.

42. Transdermal therapeutic system in accordance with any one of items 35 to 41, wherein rotigotine base is present in an amount of 1% to 30% of said dried biphasic layer.

43. Transdermal therapeutic system in accordance with any one of items 35 to 42, wherein rotigotine base is present in an amount of 10% to 26% of said dried biphasic layer, preferably of 16% to 26% of said dried biphasic layer.

44. Transdermal therapeutic system in accordance with any one of items 35 to 43, wherein rotigotine base is present in an amount of 16% to 30% of said dried biphasic layer.

45. Transdermal therapeutic system in accordance with any one of items 1 to 44, wherein the dried biphasic layer has an area weight of about 30 g/m$^2$ to about 200 g/m$^2$.

46. Transdermal therapeutic system in accordance with any one of items 1 to 45, wherein the dried biphasic layer has an area weight of about 100 g/m$^2$ to about 200 g/m$^2$.

47. Transdermal therapeutic system in accordance with any one of items 1 to 46, wherein the biphasic layer has an area weight of about 100 g/m$^2$ to about 200 g/m$^2$ and wherein rotigotine base is present in an amount of 16% to 26% of said biphasic layer.

48. Transdermal therapeutic system in accordance with any one of items 1 to 47, wherein the dried biphasic layer comprises an anti-oxidant selected from the group consisting of sodium metabisulfite, ascorbyl palmitate, tocopherol and esters thereof, ascorbic acid, butylhydroxytoluene, butylhydroxyanisole or propyl gallate.

49. Transdermal therapeutic system in accordance with any one of items 1 to 48, wherein the skin contact layer has a pressure-sensitive adhesive composition comprising pressure-sensitive polymers selected from polysiloxanes, or polyisobutylenes.

50. Transdermal therapeutic system in accordance with any one of items 1 to 49, wherein the skin contact layer has a pressure-sensitive adhesive composition comprising pressure-sensitive adhesive polysiloxane.

51. Transdermal therapeutic system in accordance with any one of items 1 to 50, wherein the skin contact layer is manufactured active agent-free or active agent-containing.

52. Transdermal therapeutic system in accordance with any one of items 1 to 51 providing a maximum droplet size of the dispersed deposits of 5 µm to 25 µm.

53. Transdermal therapeutic system in accordance with any one of items 1 to 52, wherein therapeutically effective amounts of the systemically active agent are provided for 1 to 7 days by said transdermal therapeutic system during an administration period on the skin of a human patient of 1 to 7 days.

54. Transdermal therapeutic system in accordance with any one of items 1 to 53, wherein therapeutically effective amounts of the systemically active agent are provided for 3 days by said transdermal therapeutic system during an administration period on the skin of a human patient of 3 days.

55. Transdermal therapeutic system in accordance with any one of items 1 to 54, wherein therapeutically effective amounts of the systemically active agent are provided for 4 days by said transdermal therapeutic system during an administration period on the skin of a human patient of 4 days.

56. Transdermal therapeutic system in accordance with any one of items 1 to 55, wherein therapeutically effective amounts of the systemically active agent are provided for 7 days by said transdermal therapeutic system during an administration period on the skin of a human patient of 7 days.

57. Transdermal therapeutic system in accordance with any one of items 1 to 56 for use in a method of treatment.

58. Transdermal therapeutic system in accordance with any one of items 35 to 57 for use in a method of treating patients suffering from Parkinson's disease, Parkinson's plus syndrome, depression, anxiety, attention deficit/hyperactivity syndrome, fibromyalgia, the restless-legs syndrome and for use in the treatment or prevention of dopaminergic neuron loss or the treatment or prevention of cognitive disorders, dementia or lewy body disease.

59. Use of an interface mediator other than silicone oil to reduce the maximum droplet size of the dispersed deposits of a transdermal therapeutic system in accordance with any one of items 1 to 58.

60. Use of an interface mediator other than silicone oil in a transdermal therapeutic system with an active agent-containing dried biphasic layer having a hydrophilic inner phase and a hydrophobic outer phase for controlling the maximum droplet size of the inner phase of said dried biphasic layer.

61. Use of an interface mediator other than silicone oil in a transdermal therapeutic system according to any one of items 1 through 60, wherein the active agent is rotigotine base and is present in the dried biphasic layer in an amount of 16% to 25% of the dried biphasic layer.

62. Method of manufacture of an active agent-containing dried biphasic layer comprising the steps of:
  (1) preparing a biphasic coating mixture having an inner phase dispersed in an outer phase:
    (a) the inner phase comprising the active agent,
    (b) the outer phase comprising a polymer or polymer mixture,
    wherein the biphasic coating mixture comprises solvents in sufficient amounts to provide for a viscosity of the coating mixture suitable for coating,
  (2) adding to said biphasic coating mixture an interface mediator other than silicone oil, and mixing said coating mixture to provide a suitable dispersion of the inner phase in the outer phase,
  (3) coating said coating mixture on a film to provide a layer of said solvent-containing mixture,
  (4) evaporating said solvents to provide a dried layer with a coating weight to provide said active agent-containing dried biphasic layer with the desired area weight,
  (5) optionally laminating two or more of said dried layers to provide said active agent-containing dried biphasic layer with the desired area weight.

63. Dried biphasic layer obtainable by a process in accordance with item 63.

64. Method of manufacture of a transdermal therapeutic system in accordance with any one of items 1 to 58 comprising an active agent-containing dried biphasic layer comprising the steps of:

(1) preparing a biphasic coating mixture having an inner phase dispersed in an outer phase:
  (a) the inner phase comprising the active agent,
  (b) the outer phase comprising a polymer or polymer mixture,
  wherein the biphasic coating mixture comprises solvents in sufficient amounts to provide for a viscosity of the coating mixture suitable for coating,
(2) adding to said biphasic coating mixture an interface mediator other than silicone oil, and
  mixing said coating mixture to provide a suitable dispersion of the inner phase in the outer phase,
(3) coating said coating mixture on a film to provide a layer of said solvent-containing mixture,
(4) evaporating said solvents to provide a dried layer with a coating weight to provide an active agent-containing dried biphasic layer with the desired area weight,
(5) optionally laminating two or more of said dried layers to provide an active agent-containing dried biphasic layer with the desired area weight,
(6) laminating said active agent-containing dried biphasic layer to a backing layer,
(7) optionally laminating said active agent-containing biphasic layer to an additional skin contact layer.

65. Transdermal therapeutic system obtainable by a process in accordance with item 64.

66. Transdermal therapeutic system for the transdermal administration of a rotigotine containing 2.0 mg/cm$^2$ to 4.0 mg/cm$^2$ rotigotine base in a self-adhesive layer structure, comprising
  A) a backing layer, and
  B) a dried biphasic layer, the dried biphasic layer having
    a) an outer phase having a composition comprising 75% to 100% of pressure-sensitive adhesive polysiloxane(s), and
    b) an inner phase having a composition comprising rotigotine base,
    wherein the inner phase forms dispersed deposits in the outer phase, and
    c) 0.1% to 3.5% of an interface mediator other than silicone oil with a kinematic viscosity of from 10 cSt to 100 000 cSt at 25° C.,
  and
  C) optionally an additional skin contact layer.

67. Transdermal therapeutic system for the transdermal administration of rotigotine containing 2.0 mg/cm$^2$ to 3.0 mg/cm$^2$ rotigotine base in a self-adhesive layer structure, comprising
  A) a backing layer, and
  B) a dried biphasic layer, the dried biphasic layer having
    a) an outer phase having a composition comprising 75% to 100% of pressure-sensitive adhesive polysiloxane(s), and
    b) an inner phase having a composition comprising rotigotine base,
    wherein the inner phase forms dispersed deposits in the outer phase, and
    c) 0.1% to 3.5% of an interface mediator other than silicone oil with a kinematic viscosity of from 10 cSt to 100 000 cSt at 25° C.,
  and
  C) optionally an additional skin contact layer,
for use in a method of treatment providing therapeutically effective amounts of rotigotine base for 7 days by said transdermal therapeutic system during an administration period on the skin of a human patient of 7 days.

68. Transdermal therapeutic system for the transdermal administration of rotigotine containing 2.0 mg/cm$^2$ to 3.0 mg/cm$^2$ rotigotine base in a self-adhesive layer structure, comprising
  A) a backing layer, and
  B) a dried biphasic layer, the dried biphasic layer having
    a) an outer phase having a composition comprising 75% to 100% of pressure-sensitive adhesive polysiloxane(s), and
    b) an inner phase having a composition comprising rotigotine base,
    wherein the inner phase forms dispersed deposits in the outer phase, and
    c) 0.1% to 3.5% of an interface mediator other than silicone oil with a kinematic viscosity of from 10 cSt to 100 000 cSt at 25° C.,
  and
  C) optionally an additional skin contact layer,
for use in a method of treatment of patients suffering from Parkinson's disease, Parkinson's plus syndrome, depression, anxiety, attention deficit/hyperactivity syndrome, fibromyalgia, the restless-legs syndrome and for use in the treatment or prevention of dopaminergic neuron loss or the treatment or prevention of cognitive disorders, dementia or lewy body disease by providing therapeutically effective amounts of rotigotine base for 7 days by said transdermal therapeutic system during an administration period on the skin of a human patient of 7 days.

That which is claimed:

1. A transdermal therapeutic system for the transdermal administration of at least one systemically active agent comprising a self-adhesive layer structure, said transdermal therapeutic system comprising
  A) a backing layer, and
  B) a dried biphasic layer, the dried biphasic layer having
    a) an outer phase having a composition comprising 75% to 100% of a polymer or a polymer mixture having a dynamic viscosity above 150 Pas at a temperature of 160° C., and
    b) an inner phase having a composition comprising the at least one active agent wherein the inner phase forms dispersed deposits in the outer phase,
    and
    c) 0.1% to 3.5% of an interface mediator other than silicone oil with a kinematic viscosity of from 10 cSt to 100 000 cSt at 25° C.,
  and
  C) optionally an additional skin contact layer,
    wherein the outer phase is hydrophobic, the inner phase is hydrophilic and the interface mediator is hydrophobic and
    the inner phase and outer phase define an interface and the interface mediator fills cavities at the interface between the inner phase and outer phase,
    wherein the at least one active agent is selected from the group of rotigotine, fentanyl, oxybutynine, and fesoterodine, and
    the dispersed deposits have a maximum droplet size of 5 μm to 25 μm.

2. The transdermal therapeutic system in accordance with claim 1, wherein said outer phase is a pressure-sensitive adhesive composition.

3. The transdermal therapeutic system in accordance with claim 1, wherein the hydrophobic polymer or polymer mixture is a/are pressure-sensitive adhesive polysiloxane(s).

4. The transdermal therapeutic system in accordance with claim 1, wherein the inner phase comprises a hydrophilic agent and the at least one systemically active agent forms a solid solution with the hydrophilic agent.

5. The transdermal therapeutic system in accordance with claim 4, wherein the hydrophilic agent in the inner phase is a hydrophilic polymer or polymer mixture.

6. The transdermal therapeutic system in accordance with claim 5, wherein the hydrophilic polymer or polymer mixture in the inner phase is a/are polyvinylpyrrolidone(s).

7. The transdermal therapeutic system in accordance with claim 1, wherein the interface mediator exhibits a kinematic viscosity of about 100 cSt to about 30 000 cSt.

8. The transdermal therapeutic system in accordance with claim 1, wherein the at least one active agent is rotigotine base or a pharmaceutically acceptable salt thereof.

9. The transdermal therapeutic system in accordance with claim 1, wherein the skin contact layer is a pressure-sensitive adhesive composition comprising pressure-sensitive adhesive polysiloxane.

10. The transdermal therapeutic system in accordance with claim 1, wherein the skin contact layer is manufactured active agent-free or active agent-containing.

11. The transdermal therapeutic system in accordance with claim 1, wherein the system comprises therapeutically effective amounts of the at least one systemically active agent sufficient for 1 to 7 days during an administration period on a human patient's skin of 1 to 7 days.

12. The transdermal therapeutic system in accordance with claim 11, wherein therapeutically effective amounts of the at least one systemically active agent are provided 7 days by said transdermal therapeutic system during an administration period on the skin of a human patient of 7 days.

13. The transdermal therapeutic system in accordance with claim 1, wherein the at least one active agent is rotigotine base, present in the dried biphasic layer in an amount of 16% to 26% of the dried biphasic layer.

14. A method of treating patients suffering from Parkinson's disease or Parkinson's plus syndrome comprising administering the transdermal therapeutic system as claimed in claim 1.

15. An interface mediator comprising a hydrophobic agent other than silicone oil within a hydrophobic outer phase, said interface mediator reducing the dispersed deposit maximum droplet size within the transdermal therapeutic system in accordance with claim 1.

16. The interface mediator according to claim 15, wherein the transdermal therapeutic system comprises the at least one systemically active agent-containing dried biphasic layer having the hydrophilic inner phase and the hydrophobic outer phase and the maximum droplet size of the inner phase of said dried biphasic layer is controlled via the interface mediator.

17. A transdermal therapeutic system for the transdermal administration of rotigotine containing 2.0 mg/cm$^2$ to 4.0 mg/cm$^2$ rotigotine base in a self-adhesive layer structure, comprising
A) a backing layer, and
B) a dried biphasic layer, the dried biphasic layer having
  a) a hydrophobic outer phase having a composition comprising 75% to 100% of pressure-sensitive adhesive polysiloxane(s), and
  b) a hydrophillic inner phase having a composition comprising rotigotine base, wherein the inner phase forms dispersed deposits in the outer phase, and
  c) 0.1% to 3.5% of a hydrophobic interface mediator other than silicone oil with a kinematic viscosity of from 10 cSt to 100 000 cSt at 25° C.,
and
C) optionally an additional skin contact layer,
  wherein the polysiloxanes have a solution viscosity at 25° C. and 60% solids content in heptane from greater than 150 mPa s to about 700 mPa s,
  the inner phase and outer phase define an interface and the interface mediator fills cavities at the interface between the inner phase and outer phase,
  and the dispersed deposits have a maximum droplet size of 5 µm to 25 µm.

18. The transdermal therapeutic system for the transdermal administration of rotigotine according to claim 17, wherein said transdermal therapeutic system contains 2.0 mg/cm$^2$ to 3.0 mg/cm$^2$ rotigotine base in a therapeutically effective amount to administer rotigotine base for 7 days during an administration period of the transdermal therapeutic system on a human patient's skin of 7 days.

19. The transdermal therapeutic system for the transdermal administration of rotigotine according to claim 18, wherein the therapeutically effective amount is the therapeutically effective amount to treat patients suffering from Parkinson's disease or Parkinson's plus syndrome for 7 days during an administration period of the transdermal therapeutic system on the skin of a human patient of 7 days.

* * * * *